US012786311B2

(12) United States Patent
Lee et al.

(10) Patent No.: US 12,786,311 B2

(45) Date of Patent: Nov. 3, 2026

(54) ELECTRONIC DEVICE PERFORMING OPERATION ACCORDING TO SLEEP PHASE AND OPERATING METHOD FOR ELECTRONIC DEVICE

(71) Applicant: SAMSUNG ELECTRONICS CO., LTD., Suwon-si (KR)

(72) Inventors: Hwajun Lee, Suwon-si (KR); Seungwook Nam, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 397 days.

(21) Appl. No.: 18/103,799

(22) Filed: Jan. 31, 2023

(65) Prior Publication Data

US 2023/0171341 A1 Jun. 1, 2023

Related U.S. Application Data

(63) Continuation of application No. PCT/KR2021/009961, filed on Jul. 30, 2021.

(30) Foreign Application Priority Data

Jul. 31, 2020 (KR) ........................ 10-2020-0096416

(51) Int. Cl.

*H04M 1/72463* (2021.01)
*A61B 5/00* (2006.01)
(Continued)

(52) U.S. Cl.

CPC ..... *H04M 1/724634* (2022.02); *A61B 5/4812* (2013.01); *G06F 21/32* (2013.01); *H04M 1/72469* (2021.01); *H04M 1/72484* (2021.01)

(58) Field of Classification Search

CPC ........ H04M 1/724634; H04M 1/72484; A61B 5/4812; G06F 21/32
See application file for complete search history.

(56) References Cited

U.S. PATENT DOCUMENTS

| | | | |
|---|---|---|---|
| 9,094,539 | B1 | 7/2015 | Noble |
| 10,616,167 | B2 | 4/2020 | Ganesh et al. |

(Continued)

FOREIGN PATENT DOCUMENTS

| | | | |
|---|---|---|---|
| CN | 105657186 | A | 6/2016 |
| CN | 103929835 | B | 8/2017 |

(Continued)

OTHER PUBLICATIONS

Korean Office Action corresponding to Application No. 10-2020-0096416, Dated Mar. 19, 2025.

(Continued)

*Primary Examiner* — Curtis B Odom
(74) *Attorney, Agent, or Firm* — CANTOR COLBURN LLP

(57) ABSTRACT

An electronic device according to an embodiment of the present disclosure comprises: a display for displaying a screen; a memory; and a processor electrically connected to the display and the memory, wherein the processor acquires sleep data from an external electronic device, determines a sleep phase on the basis of the acquired sleep data, identifies an operation mode of the electronic device associated with the determined sleep phase, and when the operation mode is identified, sets the electronic device to the identified operation mode. According to various embodiments of the present disclosure, it is possible to solve the inconveniences of resetting the mode of the electronic device depending on sleep and wake status. In addition, it is possible to prevent the problem of allowing other people to view potentially sensitive information such as the content of notifications while sleeping or missed calls during absence, or otherwise unintentionally leaking important information.

20 Claims, 15 Drawing Sheets

(51) Int. Cl.
*G06F 21/32* (2013.01)
*H04M 1/72469* (2021.01)
*H04M 1/72484* (2021.01)

(56) References Cited

U.S. PATENT DOCUMENTS

| | | | | |
|---|---|---|---|---|
| 11,194,297 | B2 | 12/2021 | Xie | |
| 2014/0347366 | A1 | 11/2014 | Emori et al. | |
| 2016/0142407 | A1 | 5/2016 | Chun et al. | |
| 2016/0202834 | A1 | 7/2016 | Jiang et al. | |
| 2016/0235359 | A1 | 8/2016 | Cho et al. | |
| 2017/0087330 | A1* | 3/2017 | Kahn | A61B 5/6824 |
| 2017/0092111 | A1 | 3/2017 | Hou et al. | |
| 2017/0118642 | A1 | 4/2017 | Fukui et al. | |
| 2017/0143252 | A1 | 5/2017 | Zou et al. | |
| 2017/0302773 | A1 | 10/2017 | Okamoto et al. | |
| 2018/0157817 | A1* | 6/2018 | Gao | G06F 21/35 |
| 2019/0045046 | A1 | 2/2019 | Ma | |
| 2021/0373504 | A1* | 12/2021 | Watanabe | A61M 21/00 |

FOREIGN PATENT DOCUMENTS

| | | | |
|---|---|---|---|
| CN | 107635074 | A | 1/2018 |
| CN | 107944242 | A | 4/2018 |
| JP | 5870706 | B2 | 3/2016 |
| JP | 6060240 | B1 | 1/2017 |
| JP | 2017513154 | A | 5/2017 |
| JP | 2017195445 | A | 10/2017 |
| JP | 6267025 | B2 | 1/2018 |
| KR | 20070000848 | A | 1/2007 |
| KR | 20160006437 | A | 1/2016 |
| KR | 20160057837 | A | 5/2016 |
| KR | 20160099423 | A | 8/2016 |
| KR | 20170026893 | A | 3/2017 |
| KR | 20170048233 | A | 5/2017 |
| KR | 20170057038 | A | 5/2017 |
| KR | 20170073548 | A | 6/2017 |
| KR | 1020170074364 | A | 6/2017 |
| KR | 1020170074372 | A | 6/2017 |
| KR | 101768524 | B1 | 8/2017 |

OTHER PUBLICATIONS

International Search Report and Written Opinion for International Application No. PCT/KR2021/009961; International Filing Date Jul. 30, 2021; Date of Mailing Nov. 26, 2021; 54 Pages.

Smart Watch Heart Rate Sensor Rate Measurement Principle (Apple Watch, Galaxy Watch); (Link: https://nhj12311.tistory.com/153), 4 pgs.

The Next Apple Watch Could Be Identified by Heart Rate; (Link: https://www.betanews.net/article/646743); 2 pgs.

Track Your Heart Rate with Apple Watch; (Link: https://support.apple.com/ko-kr/HT204666); 3 pgs.

* cited by examiner (410)

(420)

(430)

ELECTRONIC DEVICE PERFORMING OPERATION ACCORDING TO SLEEP PHASE AND OPERATING METHOD FOR ELECTRONIC DEVICE

CROSS-REFERENCE TO RELATED APPLICATION

This application is a continuation application, claiming priority under § 365(c), of an International Application No. PCT/KR2021/009961, filed on Jul. 30, 2021, which is based on and claims the benefit of a Korean patent application number 10-2020-0096416, filed on Jul. 31, 2020, in the Korean Intellectual Property Office, the disclosure of which is incorporated by reference herein in its entirety.

TECHNICAL FIELD

The disclosure relates to an electronic device performing different operations according to a sleep phase, and an operating method for the same electronic device.

BACKGROUND ART

Users of an electronic device can personalize the use of the electronic device by configuring a notification sound mode as a “Sound” mode or a “Vibrate” mode to change device behavior when normally receiving a notification, and can further personalize the electronic device by configuring the same as a “Mute” mode so as not to be distracted during sleep.

Specifically, technologies for increasing users’ convenience in a case where the users get distracted during sleep due to a notification configuration of an electronic device, or a case of changing the notification configuration of the electronic device according to a situation have been proposed.

According to the conventional art, a user may not receive a notification during sleep, the user may change a mode to an active mode again when the user uses an electronic device which is in a sleep mode, or the user may turn off the notification of the electronic device and change the mode to a vibration mode during sleep.

Technical Problem

According to the conventional art, it is inconvenient for users to configure a sound mode as a “Mute” mode so as not to be distracted during sleep, and to reconfigure the sound mode as a “Sound” mode or a “Vibrate” mode again after the users wake up.

In addition, according to the conventional art, during sleep, other people may look at information such as the content of a notification or missed calls, or important information could be unintentionally exposed to other people.

Accordingly, users have demanded technologies which can prevent a security accident such as a case where other people look at the content of an electronic device, or can solve a problem of inconvenience in repeating reconfiguration of the electronic device according to a situation.

Solution to Problem

An electronic device according to an embodiment of the disclosure may include a display configured to display a screen, a memory, and a processor electrically connected to the display and the memory, wherein the processor is configured to acquire sleep data from an external electronic device, determine a sleep phase, based on the acquired sleep data, identify an operation mode of the electronic device, the operation mode being associated with the determined sleep phase, and in case that the operation mode is identified, configure the electronic device with the identified operation mode.

An operation method of an electronic device according to an embodiment of the disclosure may include acquiring sleep data from an external electronic device, determining a sleep phase, based on the acquired sleep data, identifying an operation mode of the electronic device, the operation mode being associated with the determined sleep phase, and in case that the operation mode is identified, configuring the electronic device with the identified operation mode.

Advantageous Effects of Invention

According to various embodiments of the disclosure, a problem of inconvenience in reconfiguring a mode of an electronic device according to a situation where a user goes to sleep or wakes up can be solved.

According to various embodiments, a problem that other people can look at unintentionally exposed information such as the content of a notification or missed calls or important information during sleep can be prevented.

Effects which can be achieved based on various embodiments are not limited to the above-mentioned effects, and other unmentioned effects can be apparently understood from the deception below by those skilled in the art to which the disclosure belongs.

BEST MODE FOR CARRYING OUT THE INVENTION

Figure 1:
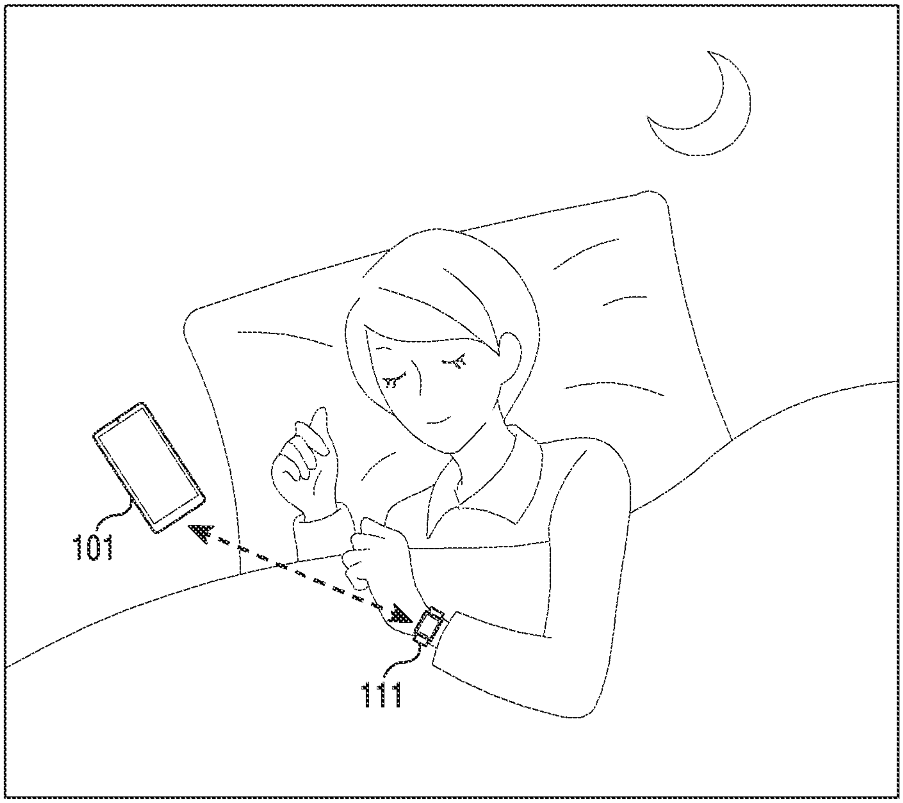
FIG. 1 illustrates a system including an electronic device and an external device performing an operation according to a sleep phase based on sleep data of a user according to various embodiments.

FIG. 1 illustrates a system including an electronic device and an external device performing an operation according to a sleep phase based on sleep data of a user according to various embodiments.

In an embodiment, a user may be sleeping while wearing an external electronic device 111 and not controlling an electronic device 101. For example, the external electronic device 111 may be a wearable device such as a smart watch, a smart band, and an activity tracker, and the user may be sleeping while wearing the external electronic device 111. In another example, the external electronic device 111 may be a device such as a small sensor or a sleeping pad mounted on a pillow, and in this case, the user may not be wearing the external electronic device 111.

In an embodiment, the external electronic device 111 may acquire sleep data relating to a sleep phase of a user while the user is sleeping. For example, the external electronic device 111 may acquire sleep data relating a sleep phase by measuring a heart rate of the user by using a photoplethysmography scheme. In addition, the external electronic device 111 may distinguish the degree (or the depth) of a sleeping state of the user, based on the acquired sleep data.

In an embodiment, the external electronic device 111 may distinguish the degree of a sleeping state of the user, at least based on a cardiac cycle, a heart rate, and regularity of cardiac rhythm, and distinguish a sleep phase (e.g., a sleep-entering phase, a first sleep phase, and a second sleep phase or later) of the user. For example, the sleep-entering phase corresponds to a state in which the user tries to go to sleep, and may be a state in which the user has been asleep for only a short time, or a state of light sleeping and/or having a dream (e.g., REM sleep). The first sleep phase may correspond to a state in which the user gets a deeper sleep than the sleep-entering phase but a lighter sleep than a deep sleep with no dreaming. The second sleep phase or later may be a state in which the user gets a deep sleep with no dreaming (e.g., delta sleep).

In an embodiment, the external electronic device 111 may share the sleep data acquired from the user with the electronic device 101, or transmit the same to the electronic device 101. The electronic device 101 may perform operations according to the sleep phase, based on the sleep data acquired from the external electronic device 111.

According to various embodiments, the electronic device 101 may correspond to an electronic device 201 to be described below.

Figure 2:
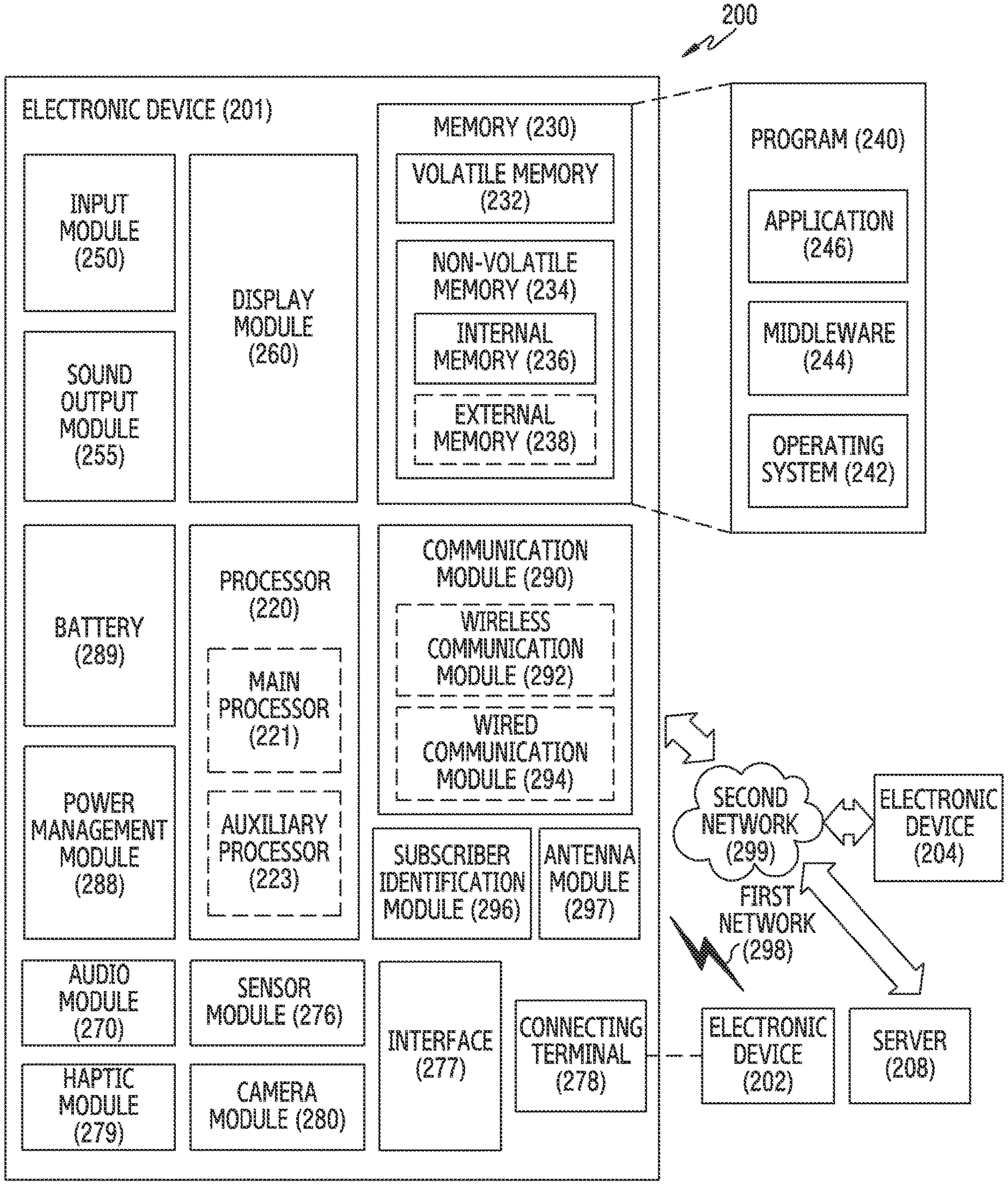
FIG. 2 is a block diagram illustrating an electronic device in a network environment according to various embodiments.

FIG. 2 is a block diagram illustrating an electronic device 201 in a network environment 200 according to various embodiments.

Referring to FIG. 2, the electronic device 201 in the network environment 200 may communicate with an external electronic device 202 via a first network 298 (e.g., a short-range wireless communication network), or at least one of an external electronic device 204 or a server 208 via a second network 299 (e.g., a long-range wireless communication network). According to an embodiment, the electronic device 201 may communicate with the external electronic device 204 via the server 208. According to an embodiment, the electronic device 201 may include a processor 220, memory 230, an input module 250, a sound output module 255, a display module 260, an audio module 270, a sensor module 276, an interface 277, a connecting terminal 278, a haptic module 279, a camera module 280, a power management module 288, a battery 289, a communication module 290, a subscriber identification module (SIM) 296, or an antenna module 297. In some embodiments, at least one of the components (e.g., the connecting terminal 278) may be omitted from the electronic device 201, or one or more other components may be added in the electronic device 201. In some embodiments, some of the components (e.g., the sensor module 276, the camera module 280, or the antenna module 297) may be implemented as a single component (e.g., the display module 260).

The processor 220 may execute, for example, software (e.g., a program 240) to control at least one other component (e.g., a hardware or software component) of the electronic device 201 coupled with the processor 220, and may perform various data processing or computation. According to one embodiment, as at least part of the data processing or computation, the processor 220 may store a command or data received from another component (e.g., the sensor module 276 or the communication module 290) in volatile memory 232, process the command or the data stored in the volatile memory 232, and store resulting data in non-volatile memory 234. According to an embodiment, the processor 220 may include a main processor 221 (e.g., a central processing unit (CPU) or an application processor (AP)), or an auxiliary processor 223 (e.g., a graphics processing unit (GPU), a neural processing unit (NPU), an image signal processor (ISP), a sensor hub processor, or a communication processor (CP)) that is operable independently from, or in conjunction with, the main processor 221. For example, when the electronic device 201 includes the main processor 221 and the auxiliary processor 223, the auxiliary processor 223 may be adapted to consume less power than the main processor 221, or to be specific to a specified function. The auxiliary processor 223 may be implemented as separate from, or as part of the main processor 221.

The auxiliary processor 223 may control at least some of functions or states related to at least one component (e.g., the display module 260, the sensor module 276, or the communication module 290) among the components of the electronic device 201, instead of the main processor 221 while the main processor 221 is in an inactive (e.g., sleep) state, or together with the main processor 221 while the main processor 221 is in an active state (e.g., executing an application). According to an embodiment, the auxiliary processor 223 (e.g., an image signal processor or a communication processor) may be implemented as part of another component (e.g., the camera module 280 or the communication module 290) functionally related to the auxiliary processor 223. According to an embodiment, the auxiliary processor 223 (e.g., the neural processing unit) may include a hardware structure specified for artificial intelligence model processing. An artificial intelligence model may be generated by machine learning. Such learning may be performed, e.g., by the electronic device 201 where the artificial intelligence is performed or via a separate server (e.g., the server 208). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 230 may store various data used by at least one component (e.g., the processor 220 or the sensor module 276) of the electronic device 201. The various data may include, for example, software (e.g., the program 240) and input data or output data for a command related thereto. The memory 230 may include the volatile memory 232 or the non-volatile memory 234.

The program 240 may be stored in the memory 230 as software, and may include, for example, an operating system (OS) 242, middleware 244, or an application 246.

The input module 250 may receive a command or data to be used by another component (e.g., the processor 220) of the electronic device 201, from the outside (e.g., a user) of the electronic device 201. The input module 250 may include, for example, a microphone, a mouse, a keyboard, a key (e.g., a button), or a digital pen (e.g., a stylus pen).

The sound output module 255 may output sound signals to the outside of the electronic device 201. The sound output module 255 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 260 may visually provide information to the outside (e.g., a user) of the electronic device 201. The display module 260 may include, for example, a display, a hologram device, or a projector and control circuitry to control a corresponding one of the display, hologram device, and projector. According to an embodiment, the display module 260 may include a touch sensor adapted to detect a touch, or a pressure sensor adapted to measure the intensity of force incurred by the touch.

The audio module 270 may convert a sound into an electrical signal and vice versa. According to an embodiment, the audio module 270 may obtain the sound via the input module 250, or output the sound via the sound output module 255 or a headphone of an external electronic device (e.g., an external electronic device 202) directly (e.g., wiredly) or wirelessly coupled with the electronic device 201.

The sensor module 276 may detect an operational state (e.g., power or temperature) of the electronic device 201 or an environmental state (e.g., a state of a user) external to the electronic device 201, and then generate an electrical signal or data value corresponding to the detected state. According to an embodiment, the sensor module 276 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 277 may support one or more specified protocols to be used for the electronic device 201 to be coupled with the external electronic device (e.g., the external electronic device 202) directly (e.g., wiredly) or wirelessly. According to an embodiment, the interface 277 may include, for example, a high definition multimedia interface (HDMI), a universal serial bus (USB) interface, a secure digital (SD) card interface, or an audio interface.

A connecting terminal 278 may include a connector via which the electronic device 201 may be physically connected with the external electronic device (e.g., the external electronic device 202). According to an embodiment, the connecting terminal 278 may include, for example, a HDMI connector, a USB connector, a SD card connector, or an audio connector (e.g., a headphone connector).

The haptic module 279 may convert an electrical signal into a mechanical stimulus (e.g., a vibration or a movement) or electrical stimulus which may be recognized by a user via his tactile sensation or kinesthetic sensation. According to an embodiment, the haptic module 279 may include, for example, a motor, a piezoelectric element, or an electric stimulator.

The camera module 280 may capture a still image or moving images. According to an embodiment, the camera module 280 may include one or more lenses, image sensors, image signal processors, or flashes.

The power management module 288 may manage power supplied to the electronic device 201. According to one embodiment, the power management module 288 may be implemented as at least part of, for example, a power management integrated circuit (PMIC).

The battery 289 may supply power to at least one component of the electronic device 201. According to an embodiment, the battery 289 may include, for example, a primary cell which is not rechargeable, a secondary cell which is rechargeable, or a fuel cell.

The communication module 290 may support establishing a direct (e.g., wired) communication channel or a wireless communication channel between the electronic device 201 and the external electronic device (e.g., the external electronic device 202, the external electronic device 204, or the server 208) and performing communication via the established communication channel. The communication module 290 may include one or more communication processors that are operable independently from the processor 220 (e.g., the application processor (AP)) and supports a direct (e.g., wired) communication or a wireless communication. According to an embodiment, the communication module 290 may include a wireless communication module 292 (e.g., a cellular communication module, a short-range wireless communication module, or a global navigation satellite system (GNSS) communication module) or a wired communication module 294 (e.g., a local area network (LAN) communication module or a power line communication (PLC) module). A corresponding one of these communication modules may communicate with the external electronic device via the first network 298 (e.g., a short-range communication network, such as Bluetooth™, wireless-fidelity (Wi-Fi) direct, or infrared data association (IrDA)) or the second network 299 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 292 may identify and authenticate the electronic device 201 in a communication network, such as the first network 298 or the second network 299, using subscriber information (e.g., international mobile subscriber identity (IMSI)) stored in the subscriber identification module 296.

The wireless communication module 292 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 292 may support a high-frequency band (e.g., the mmWave band) to achieve, e.g., a high data transmission rate. The wireless communication module 292 may support various technologies for securing performance on a high-frequency band, such as, e.g., beamforming, massive multiple-input and multiple-output (massive MIMO), full dimensional MIMO (FD-MIMO), array antenna, analog beamforming, or large scale antenna. The wireless communication module 292 may support various requirements specified in the electronic device 201, an external electronic device (e.g., the external electronic device 204), or a network system (e.g., the second network 299). According to an embodiment, the wireless communication module 292 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 297 may transmit or receive a signal or power to or from the outside (e.g., the external electronic device) of the electronic device 201. According to an embodiment, the antenna module 297 may include an antenna including a radiating element composed of a conductive material or a conductive pattern formed in or on a substrate (e.g., a printed circuit board (PCB)). According to an embodiment, the antenna module 297 may include a plurality of antennas (e.g., array antennas). In such a case, at least one antenna appropriate for a communication scheme used in the communication network, such as the first network 298 or the second network 299, may be selected, for example, by the communication module 290 (e.g., the wireless communication module 292) from the plurality of antennas. The signal or the power may then be transmitted or received between the communication module 290 and the external electronic device via the selected at least one antenna. According to an embodiment, another component (e.g., a radio frequency integrated circuit (RFIC)) other than the radiating element may be additionally formed as part of the antenna module 297.

According to various embodiments, the antenna module 297 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 201 and the external electronic device 204 via the server 208 coupled with the second network 299. Each of the external electronic devices 202 or 204 may be a device of a same type as, or a different type, from the electronic device 201. According to an embodiment, all or some of operations to be executed at the electronic device 201 may be executed at one or more of the external electronic devices 202, 204, or 208. For example, if the electronic device 201 should perform a function or a service automatically, or in response to a request from a user or another device, the electronic device 201, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 201. The electronic device 201 may provide the outcome, with or without further processing of the outcome, as at least part of a reply to the request. To that end, a cloud computing, distributed computing, mobile edge computing (MEC), or client-server computing technology may be used, for example. The electronic device 201 may provide ultra low-latency services using, e.g., distributed computing or mobile edge computing. In another embodiment, the external electronic device 204 may include an internet-of-things (IoT) device. The server 208 may be an intelligent server using machine learning and/or a neural network. According to an embodiment, the external electronic device 204 or the server 208 may be included in the second network 299. The electronic device 201 may be applied to intelligent services (e.g., smart home, smart city, smart car, or healthcare) based on 5G communication technology or IoT-related technology.

Figure 3:
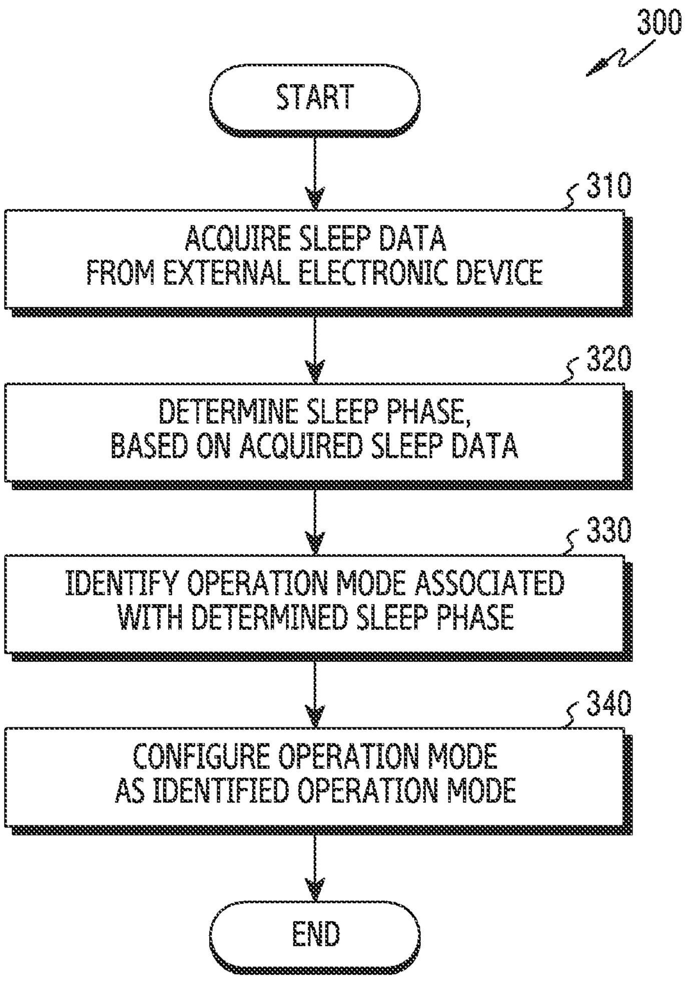
FIG. 3 is a flowchart illustrating an overall operation according to a sleep phase of an electronic device according to an embodiment.

FIG. 3 illustrates an operation according to a sleep phase of an electronic device according to an embodiment.

According to an embodiment, in operation 310, an electronic device (e.g., the electronic device 201) may acquire sleep data from an external electronic device (e.g., the external electronic device 111). For example, the external electronic device 111 may acquire sleep data which enables a sleep phase of a user to be determined while the user is sleeping. The external electronic device 111 may acquire sleep data relating to the sleep phase by measuring a heart rate of the user by using a photoplethysmography scheme. The external electronic device 111 may share (or transmit) the acquired sleep data to the electronic device 201, and the electronic device 201 may acquire the sleep data by receiving the sleep data shared (or transmitted) from the external electronic device 111.

In an embodiment, the sleep data may at least includer a cardiac cycle, a heart rate, and regularity of cardiac rhythm.

According to an embodiment, in operation 320, the electronic device (e.g., the electronic device 201) may determine a sleep phase, based on the acquired sleep data. For example, the sleep phase of the user may include a sleep-entering phase, a first sleep phase, and a second sleep phase or later (e.g., a third sleep phase, a fourth sleep phase, etc.). For example, the sleep-entering phase corresponds to a state in which the user tries to go to sleep, and may be a state in which the user has been asleep not for a long time, or a state of light sleeping and having a dream (e.g., REM sleep). In addition, the first sleep phase may correspond to a state in which the user gets a deeper sleep than the sleep-entering phase but a lighter sleep than a deep sleep with no dreaming. The second sleep phase or later may be a state in which the user gets a deep sleep with no dreaming (e.g., delta sleep). The electronic device 201 may distinguish the sleep-entering phase, the first sleep phase, and the second sleep phase or later by using the acquired sleep data (e.g., data relating to the cardiac cycle, heart rate, and regularity of cardiac rhythm), and determine the sleep phase of the user as the sleep-entering phase, the first sleep phase, or and the second sleep phase or later.

In an embodiment, the electronic device 201 may periodically receive the sleep data shared or transmitted from the external electronic device 111, and determine the sleep phase according to control by the processor 220, based on the sleep data acquired at each shared or transmitted period.

According to an embodiment, in operation 330, the electronic device (e.g., the electronic device 201) may identify an operation mode associated with the determined sleep phase according to control by the processor 220. The electronic device 201 may have an operation mode configured according to each sleep phase (e.g., the sleep-entering phase, the first sleep phase, or and the second sleep phase or later). For example, the electronic device 201 may have an operation mode relating to an alert strength, which is configured when the sleep phase of the user is the sleep-entering phase, have an operation mode relating to a notification configuration of a lock screen and a sound mode, which are configured when the sleep phase is the first sleep phase, and have an operation relating to unlocking, which is configured when the sleep phase is the second sleep phase or later. In addition, the electronic device 201 may have an operation mode configured according to a case where (i.e., responsive to) the sleep phase of the user is changed or the user wakes up. The electronic device 201 may identify an operation mode (e.g., an operation mode relating to an alert strength, a lock screen notification, a sound mode, and unlocking) associated with the sleep phase (e.g., the sleep-entering phase, the first sleep phase, or and the second sleep phase or later) determined according to the control by the processor 220.

According to an embodiment, in operation 340, the electronic device (e.g., the electronic device 201) may configure the operation mode with the identified operation mode according to control by the processor 220. For example, the electronic device 201 may configure, according to control of the processor 220, the operation mode of the electronic device 201, which relates to the alert strength, the notification on the lock screen, the sound mode, and the unlocking, as the operation mode identified in operation 330.

A more detailed description of operations 310 to 340 in FIG. 3 according to various embodiments will be made later in the necessary part.

FIG. 4 illustrates configuration of an alert strength according to a sleep phase in an electronic device according to an embodiment.

Figure 4A:
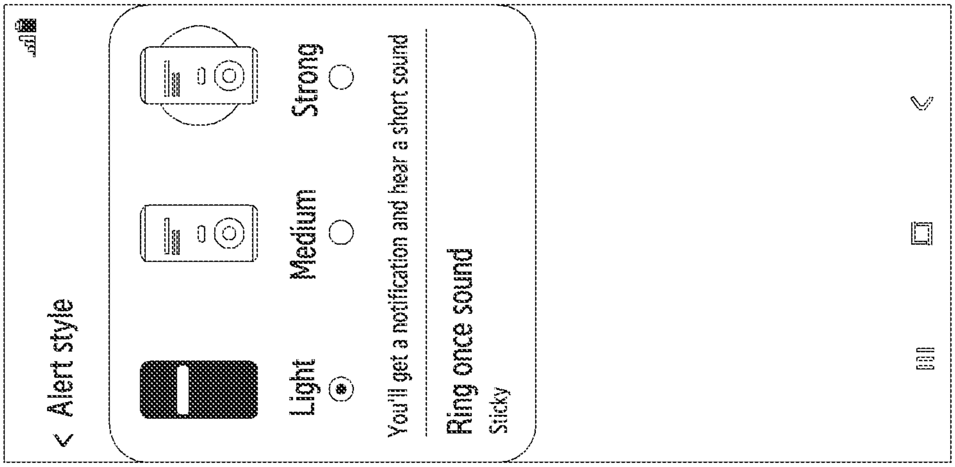
FIG. 4A illustrates a first configuration of an alert strength according to a sleep phase in an electronic device according to an embodiment.
Figure 4B:
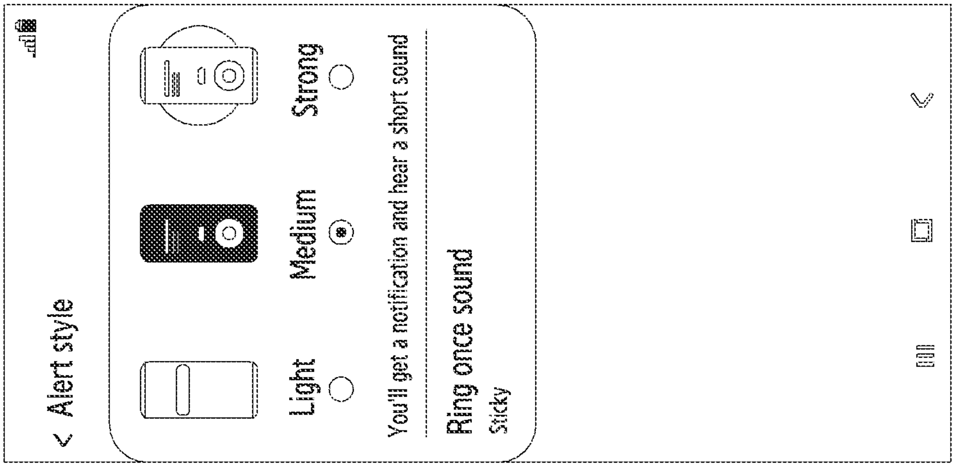
FIG. 4B illustrates a second configuration of an alert strength according to a sleep phase in an electronic device according to an embodiment.
Figure 4C:
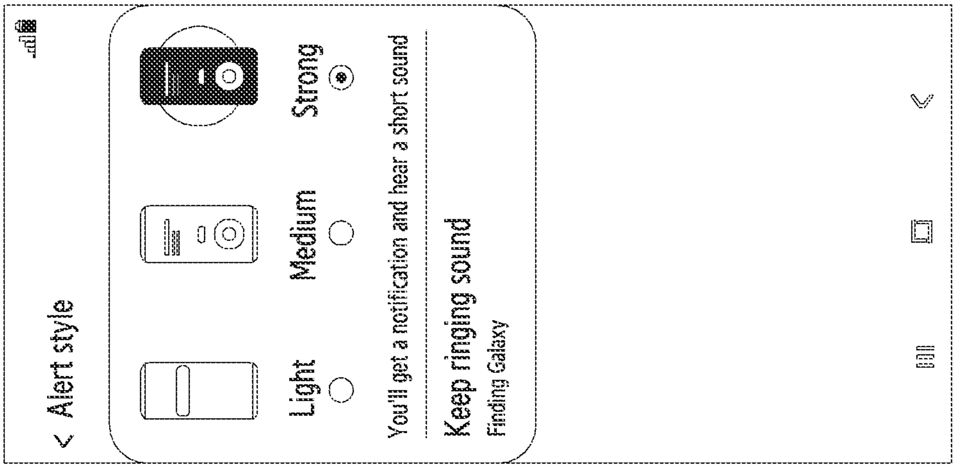
FIG. 4C illustrates a third configuration of an alert strength according to a sleep phase in an electronic device according to an embodiment.

Referring to FIGS. 4A-4C, the electronic device 201 may configure an operation mode of an alert strength from the phase entering phase or later according to control by the processor 220. For example, the operation mode of the alert strength may at least include mode 410 (FIG. 4A), mode 420 (FIG. 4B), and mode 430 (FIG. 4C). Mode 410 may correspond to a mode in which one alert is executed at a light alert strength, mode 420 may correspond to a mode in which one alert is executed at a medium alert strength, and mode 430 may correspond to a mode in which alerts are executed at a strong alert strength until a user checks.

In an embodiment, the operation mode of the alert strength of the electronic device 201 may be changed from mode 430 to mode 410 as the sleep phase proceeds from the sleep-entering phase to the second sleep phase or later. In addition, upon configuration by the user, the operation mode may be changed from mode 410 to mode 430 as the sleep phase proceeds from the sleep-entering phase to the second sleep phase or later.

In an embodiment, in relation to the operation mode of the alert strength upon the control by the processor 220 of the electronic device 201, an alert strength (e.g., a light strength, a medium strength, and a strong strength), and an alert cycle and frequency (e.g., a mode in which one alert is executed or a mode in which alerts are executed until the user checks) are not limited to the above-described example, and may be differently configured.

Figure 5:
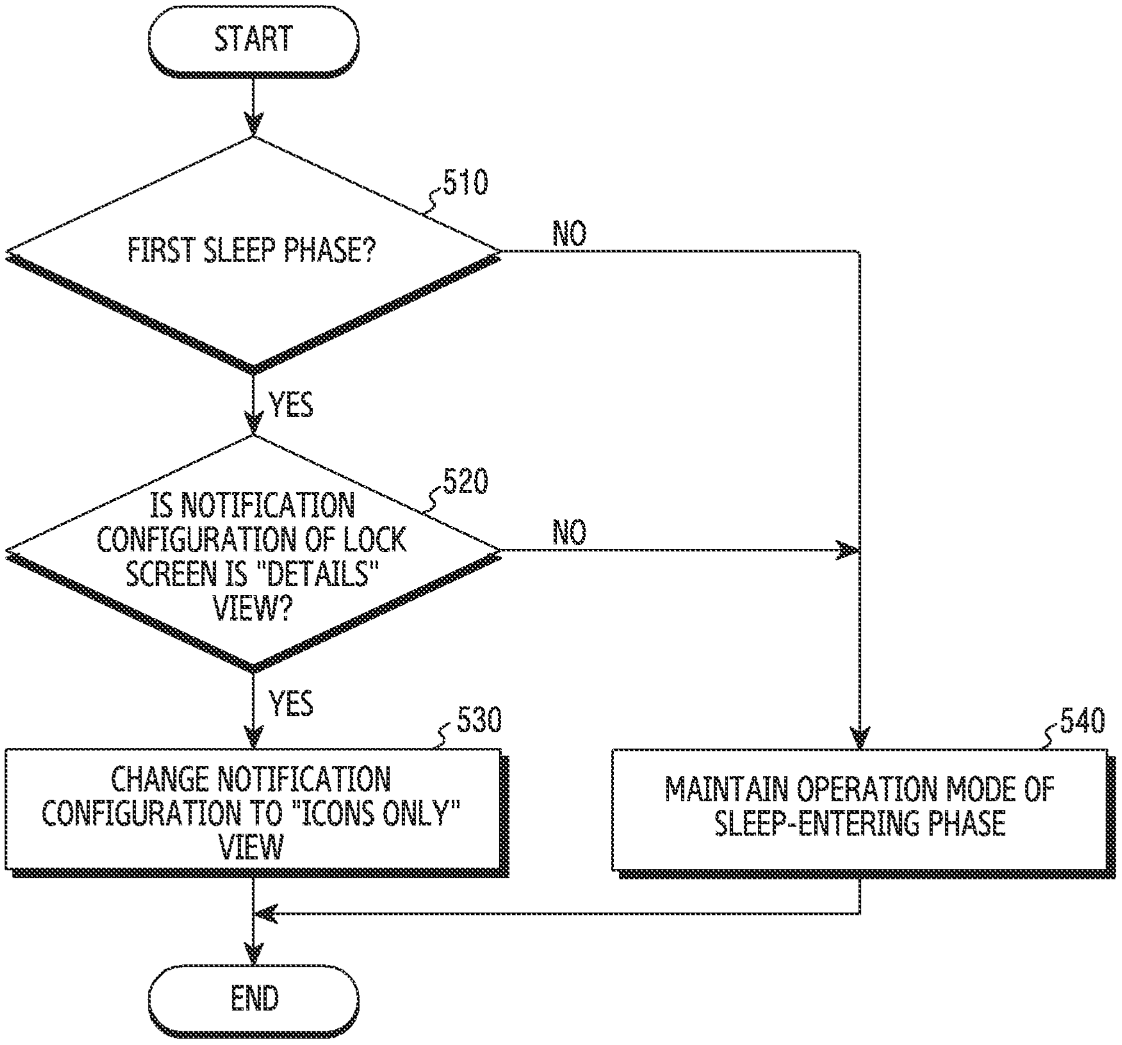
FIG. 5 is a flowchart illustrating an operation of a notification configuration of a lock screen according to a sleep phase in an electronic device according to an embodiment.

FIG. 5 is a flowchart illustrating an operation of a notification configuration of a lock screen according to a sleep phase in an electronic device according to an embodiment.

Figure 6B:
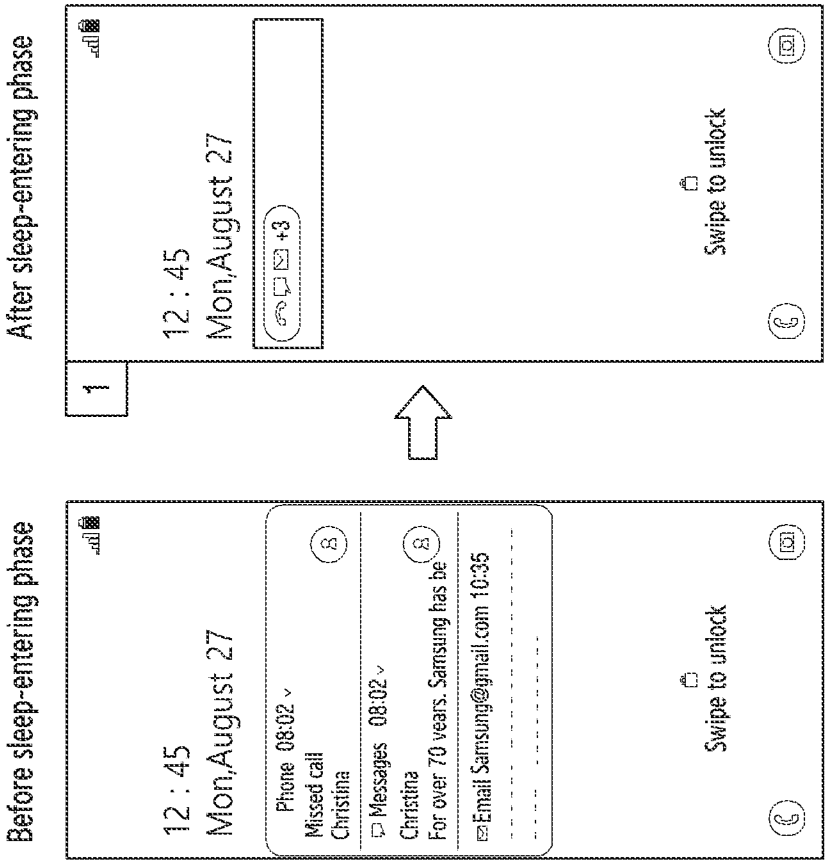
FIG. 6B illustrates a display screen of a lock screen according to a sleep phase in an electronic device.
Figure 6A:
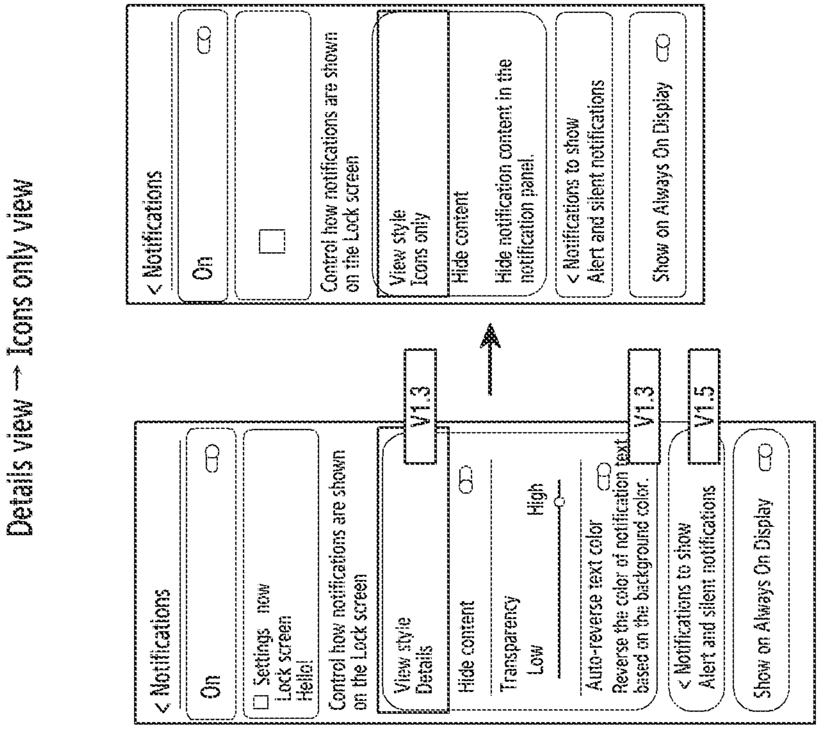
FIG. 6A illustrates a configuration screen of a notification configuration of a lock screen according to a sleep phase in an electronic device.

A description of operations 510 to 540 in FIG. 5 will be made with reference to FIGS. 6A and 6B illustrating an embodiment of a display screen of a notification configuration of a lock screen according to a sleep phase in an electronic device.

According to an embodiment, in operation 510, an electronic device (e.g., the electronic device 201) may determine whether a sleep phase of a user is a first sleep phase, according to control by the processor 220.

In an embodiment, the electronic device 201 may acquire the user's sleep data acquired by the external electronic device 111 by using the photoplethysmography scheme, according to control by the processor 220. The electronic device 201 may determine whether the sleep phase of the user is the first sleep phase, based on the acquired sleep data according to the control by the processor 220.

In an embodiment, the electronic device 201 may perform operation 520 when the sleep phase of the user is determined as the first sleep phase, according to the control by the processor 220. In addition, the electronic device 201 may perform operation 540 of maintaining the existing operation mode when the sleep phase of the user is determined as a sleep phase other than the first sleep phase (i.e., not the first sleep phase), according to the control by the processor 220.

According to an embodiment, in operation 540, the electronic device 201 may maintain, according to the control by the processor 220, the operation mode of the sleep-entering phase according to the determination that the sleep phase of the user is a sleep phase other than the first sleep phase (i.e., not the first sleep phase). For example, when the electronic device 201 has determined that the sleep phase of the user is the sleep-entering phase before, the electronic device 201 may maintain, according to the control by the processor 220, the operation mode of the existing sleep-entering phase when the determination is made that the sleep phase is not the first sleep phase.

According to an embodiment, in operation 520, the electronic device (e.g., the electronic device 201) may determine whether a notification configuration of a lock screen is a "details" view.

In an embodiment, the electronic device 201 may perform operation 530 when the notification configuration of the lock screen is determined as a "details" view, according to control by the processor 220. In addition, the electronic device 201 may perform operation 540 of maintaining the existing operation mode according to the control by the processor 220 when the notification configuration of the lock screen is determined as not a "details" view.

According to an embodiment, in operation 530, the electronic device (e.g., the electronic device 201) may change the notification configuration of the lock screen to an "icons only" view. For example, the electronic device 201 may change, according to control by the processor 220, the notification configuration of the lock screen, configured as a "details" view", to an "icons only" view corresponding to an operation mode of the lock screen in the first sleep phase. Referring to FIG. 6A, a configuration screen of the electronic device 201 may be automatically changed from the "details" view to the "icons only" view according to the control by the processor 220. Referring to FIG. 6B, a display screen of the electronic device 201 may be changed from the "details" view in which notification contents are shown in detail to the "icons only" view in which only schematic and simple notification contents are shown, according to the control by the processor 220.

Figure 7:
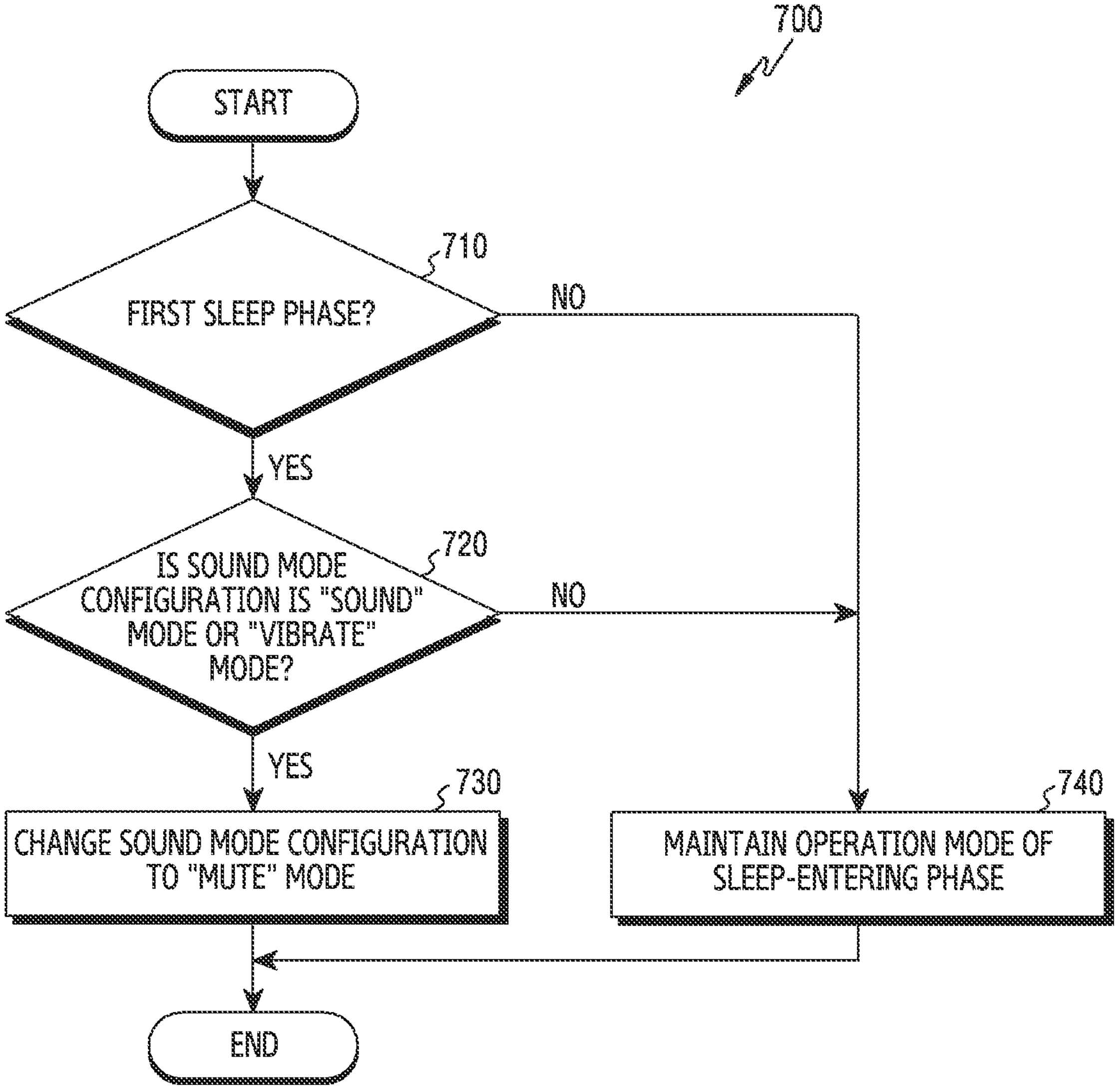
FIG. 7 is a flowchart illustrating an operation of configuration of a sound mode according to a sleep phase in an electronic device according to an embodiment.

FIG. 7 is a flowchart illustrating an operation of configuration of a sound mode according to a sleep phase in an electronic device according to an embodiment.

According to an embodiment, in operation 710, an electronic device (e.g., the electronic device 201) may determine whether a sleep phase of a user is a first sleep phase.

According to an embodiment, the electronic device 201 may acquire the user's sleep data acquired by the external electronic device 111 by using the photoplethysmography scheme. The electronic device 201 may determine whether the sleep phase of the user is the first sleep phase, based on the acquired sleep data according to control by the processor 220.

In an embodiment, the electronic device 201 may perform operation 720 according to control by the processor 220 when the sleep phase of the user is determined as the first sleep phase. In addition, the electronic device 201 may perform operation 740 of maintaining the existing operation mode when the sleep phase of the user is determined as a sleep phase other than the first sleep phase (i.e., not the first sleep phase), according to the control by the processor 220.

According to an embodiment, in operation 740, the electronic device 201 may maintain, according to the control by the processor 220, the operation mode of the sleep-entering phase according to the determination that the sleep phase of the user is not the first sleep phase. For example, when the electronic device 201 has determined that the sleep phase of the user is the sleep-entering phase before, the electronic device 201 may maintain, according to the control by the processor 220, the operation mode of the existing sleep-entering phase when determination is made that the sleep phase is not the first sleep phase.

According to an embodiment, in operation 720, the electronic device (e.g., the electronic device 201) may determine whether a sound mode configuration is a "Sound" mode or a "Vibrate" mode.

In an embodiment, the electronic device 201 may perform operation 730 according control by the processor 220 when the sound mode configuration is determined as the "Sound" mode or the "Vibrate" mode. In addition, the electronic device 201 may perform operation 740 of maintain the existing operation mode according to the control by the processor 220 when the sound mode configuration is determined as neither the "Sound" mode nor the "Vibrate" mode.

According to an embodiment, in operation 730, the electronic device (e.g., the electronic device 201) may change the sound mode configuration to a "Mute" mode. For example, the electronic device 201 may change the sound mode, configured as the "Sound" mode or the "Vibrate" mode in the sleep entering mode, to the "Mute" mode in the first sleep phase according to control by the processor 220.

According to an embodiment, in operation 740, the electronic device (e.g., the electronic device 201) may maintain an operation mode of the sleep-entering phase. For example, when the sound mode configuration of the sleep-entering phase is already configured as the "Mute" mode rather than the "Sound" mode or the "Vibrate" mode, the electronic device 201 may maintain the existing operation mode according the control by the processor 220.

Figure 8:
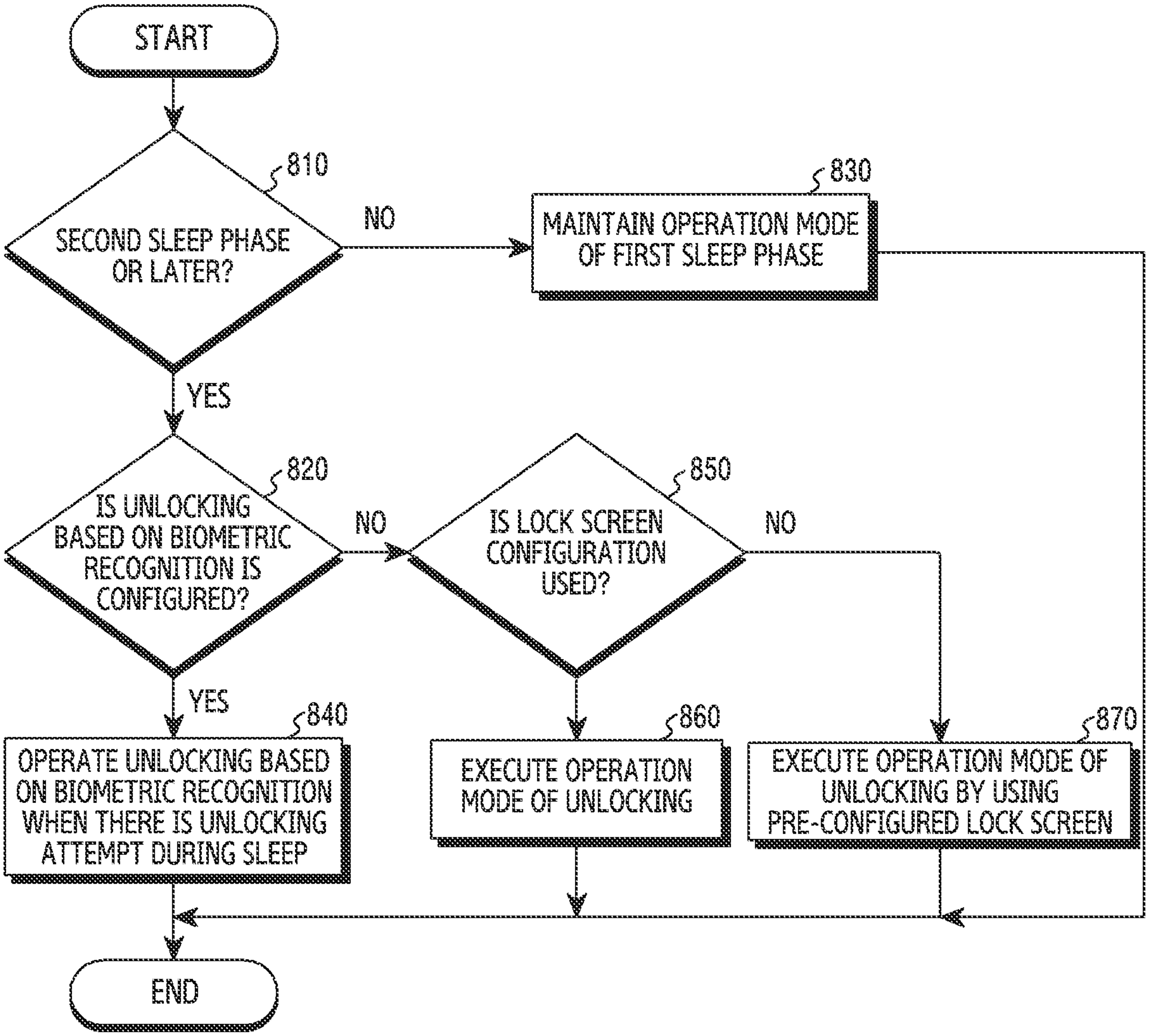
FIG. 8 is a flowchart illustrating an operation of unlocking according to a sleep phase in an electronic device according to an embodiment.
Figure 9A:
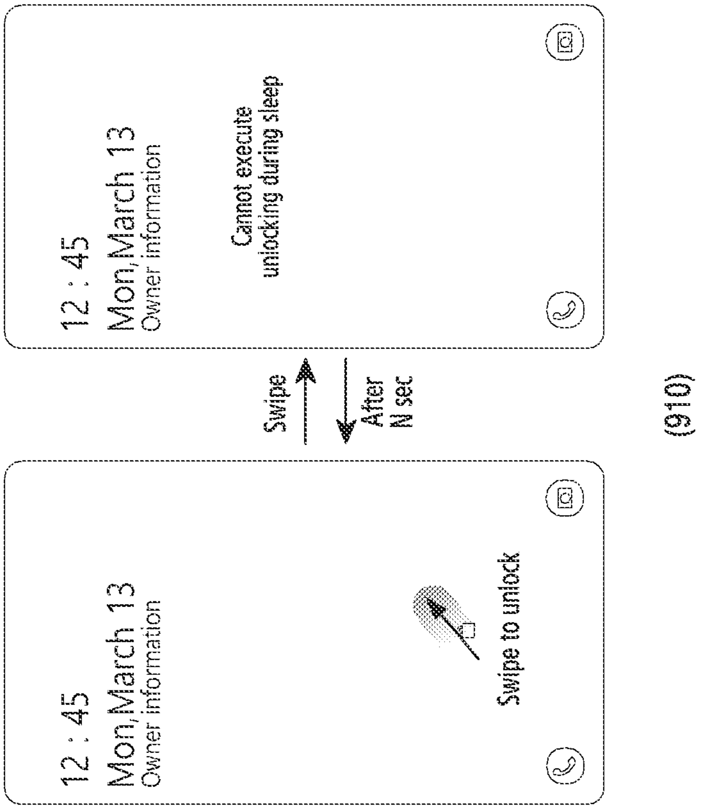
FIG. 9A illustrates a display screen before and after unlocking according to a sleep phase in an electronic device according to an embodiment.
Figure 9B:
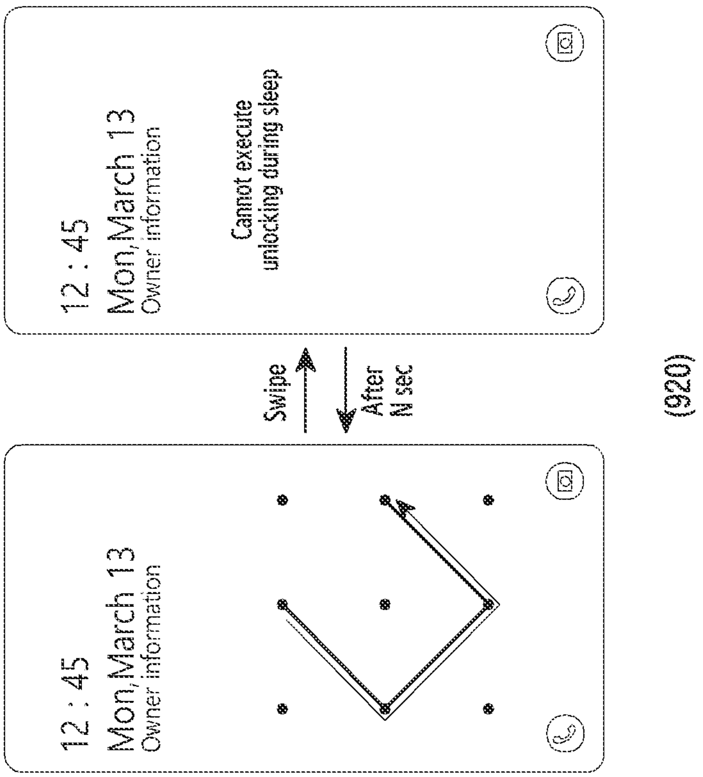
FIG. 9B illustrates a display screen before and after unlocking according to a sleep phase in an electronic device according to an embodiment.

FIG. 8 is a flowchart illustrating an operation of unlocking according to a sleep phase in an electronic device according to an embodiment. A description of operations 810 to 870 in FIG. 8 will be made with reference to FIGS. 9A and 9B illustrating an embodiment of a display screen before and after unlocking according to a sleep phase by an electronic device.

According to an embodiment, in operation 810, an electronic device (e.g., the electronic device 201) may determine whether a sleep phase of a user is a second sleep phase or later.

In an embodiment, the electronic device 201 may acquire the user's sleep data acquired by the external electronic device 111 by using the photoplethysmography scheme. The electronic device 201 may determine whether the sleep phase of the user is the second sleep phase or later, based on the acquired sleep data according to control by the processor 220.

In an embodiment, the electronic device 201 may perform operation 820 according to control by the processor 220 when the sleep phase of the user is determined as the second sleep phase or later. In addition, the electronic device 201 may perform, according to control by the processor 220, operation 830 of maintaining the existing operation mode when the sleep phase of the user is determined as a sleep phase other than the second sleep phase or any following sleep phase (i.e., not the second sleep phase or later).

According to an embodiment, in operation 830, the electronic device 201 may maintain an operation mode of the existing first sleep mode according to control by the processor 220 when the sleep phase of the user is determined as not the second sleep phase or later.

According to an embodiment, in operation 820, the electronic device (e.g., the electronic device 201) may determine whether an unlocking configuration based on biometric recognition is made.

In an embodiment, the electronic device 201 may perform, according to control by the processor 220, unlocking based on biometric recognition such as fingerprint recognition, iris recognition, or face recognition, and the unlocking based on the biometric reception may be configured by a user. The electronic device 201 may identify whether the configuration of the unlocking based on the biometric recognition is made, according to control by the processor 220.

In an embodiment, the electronic device 201 may perform operation 840 according to control by the processor 220 when whether the configuration of the unlocking based on the biometric recognition is made is identified, and may perform operation 850 according to control by the processor 220 when the configuration of the unlocking based on the biometric recognition is not made.

According to an embodiment, in operation 840, the electronic device (e.g., the electronic device 201) may operate the unlocking based on biometric recognition when there is an unlocking attempt during sleep. For example, the electronic device 201 may have identified that the unlocking configuration based on biometric recognition is made, according to control by the processor 220. Upon the identification, the electronic device 201 may perform unlocking according to control by the processor 220 when there is an unlocking attempt based on biometric recognition such as fingerprint recognition, iris recognition, and face recognition.

According to an embodiment, in operation 850, the electronic device (e.g., the electronic device 201) may determine whether a lock screen configuration is being used. For example, the electronic device 201 may determine (or identify) whether configuration of a lock screen is made, according to control by the processor 220. In addition, the electronic device 201 may perform operation 860 according to control by the processor 220 when it is identified that the configuration of the lock screen is made, and may perform operation 870 according to control by the processor 220 when it is identified that the configuration of the lock screen is not made.

According to an embodiment, in operation 860, the electronic device (e.g., the electronic device 201) may perform an operation mode of unlocking. For example, the electronic device 201 can identify according to control by the processor 220 that a lock screen is configured as shown in a lock screen 920 of FIG. 9B. The electronic device 201 may not allow unlocking to be performed when there is an unlocking attempt based on biometric recognition, according to control by the processor 220.

According to an embodiment, in operation 870, the electronic device (e.g., the electronic device 201) may execute an operation mode of unlocking by using a pre-configured lock screen according to control by the processor 220.

For example, the electronic device 201 may identify according to control by the processor 220 that there is no configuration of a lock screen as shown in a lock screen 910 of FIG. 9A. The electronic device 201 may not allow, according to control by the processor 220, unlocking to be performed by using the pre-configured lock screen when there is an unlocking attempt based on biometric recognition.

Figure 10:
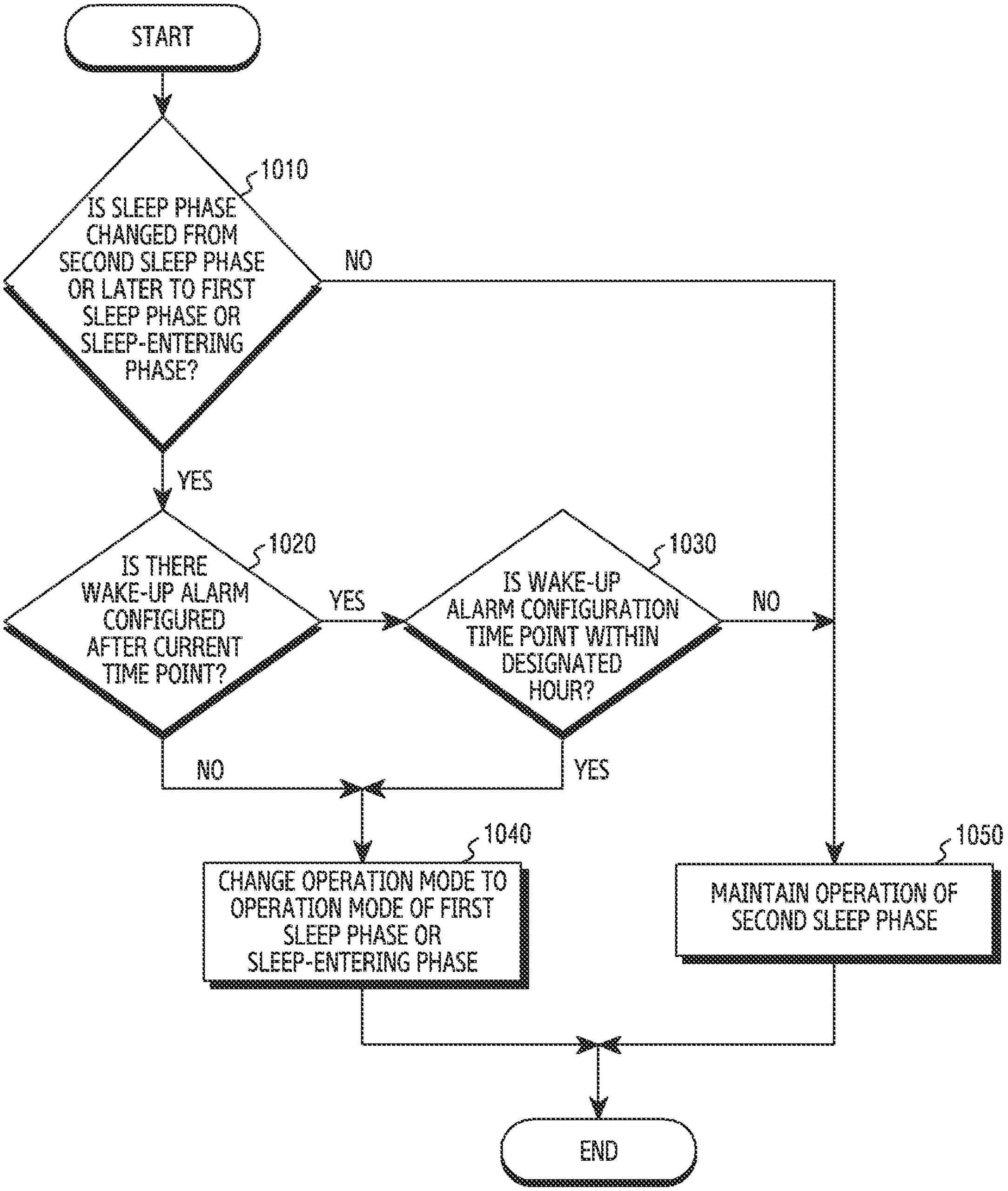
FIG. 10 is a flowchart illustrating an operation of a wake-up alarm according to a sleep phase in an electronic device according to an embodiment.
Figure 11A:
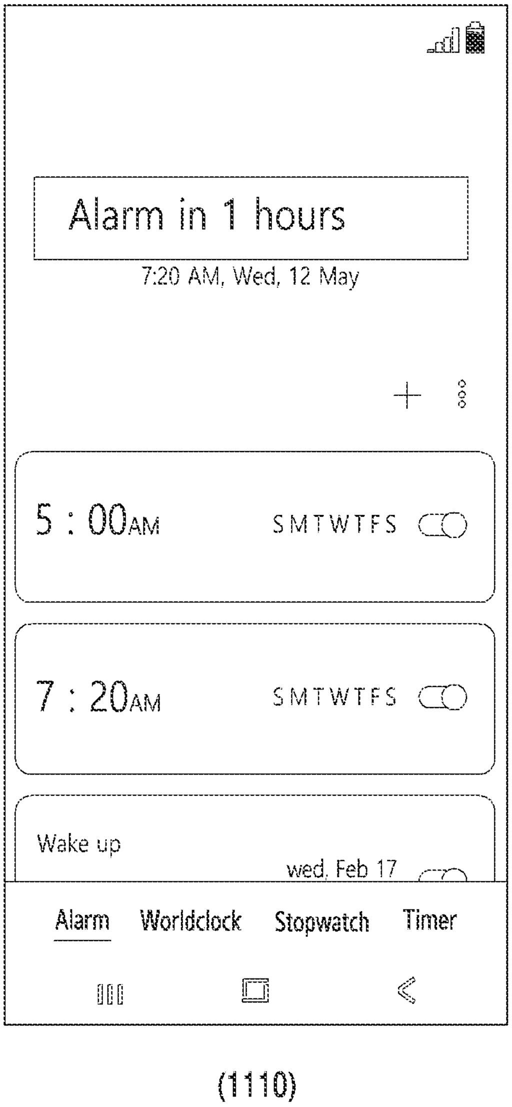
FIG. 11A illustrates a display screen of a wake-up alarm according to a sleep phase by an electronic device according to an embodiment.
Figure 11B:
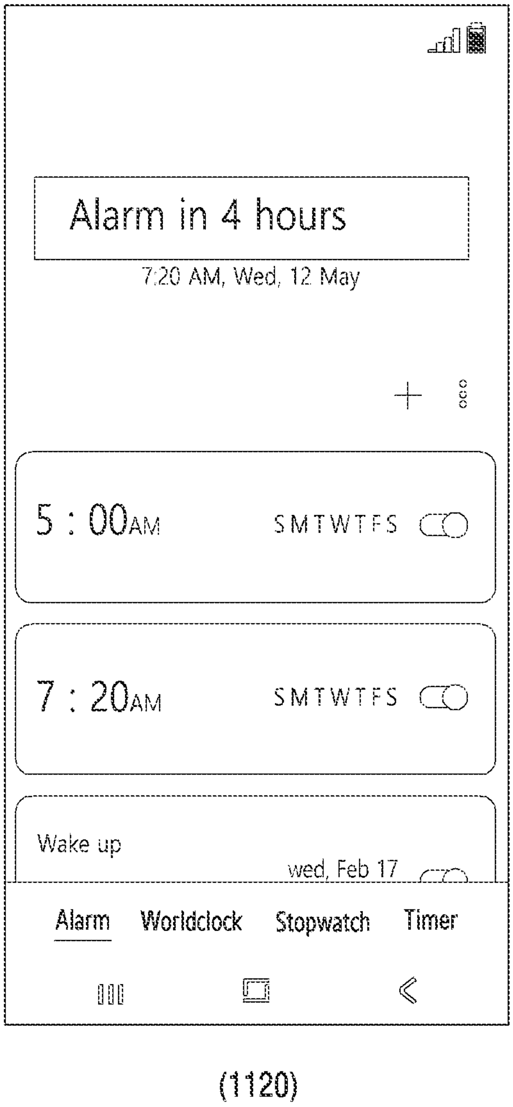
FIG. 11B illustrates a display screen of a wake-up alarm according to a sleep phase by an electronic device according to an embodiment.

FIG. 10 is a flowchart illustrating an operation of a wake-up alarm according to a sleep phase in an electronic device according to an embodiment. A description of operations 1010 to 1050 in FIG. 10 will be made with reference to FIGS. 11A and 11B illustrating a display screen of a wake-up alarm according to a sleep phase in an electronic device.

According to an embodiment, in operation 1010, an electronic device (e.g., the electronic device 201) may determine whether a sleep phase is changed from a second sleep phase or later to a first sleep phase or a sleep-entering phase.

In an embodiment, the electronic device 201 may periodically determine a sleep phase by periodically acquiring a user's sleep data from the external electronic device 111. The electronic device 201 may determine that the sleep phase of the user is the second sleep phase or later, and determine that the sleep phase of the user in the next cycle is the first sleep phase or the sleep-entering phase, according to control by the processor 220.

In an embodiment, the electronic device 201 may perform operation 1020 according to control by the processor 220 when the electronic device has determined that the sleep phase of the user is changed from the second sleep phase or later to the first sleep phase or the sleep-entering phase. In addition, the electronic device 201 may perform, according to control by the processor 220, operation 1050 of maintaining an operation of the existing sleep phase when the electronic device has determined the sleep phase of the user is not changed from the second sleep phase or later to the first sleep phase or the sleep-entering phase.

According to an embodiment, in operation 1050, the electronic device 201 may maintain an operation of the second sleep phase or later according to control by the processor 220 as the electronic device has determined that the sleep phase of the user is not changed from the second sleep phase or later to the first sleep phase or the sleep-entering phase.

According to an embodiment, in operation 1020, the electronic device (e.g., the electronic device 201) may determine whether there is a wake-up alarm configured after a current time point.

In an embodiment, the electronic device 201 may determine (or identify) according to control by the processor 220 whether there is a wake-up alarm configured after a current time point. Referring to FIG. 11A, an alarm in 1 hour with reference to a current time point may be configured as shown in an alarm screen 1110. Referring to FIG. 11B, an alarm in 4 hours with reference to a current time point may be configured as shown in an alarm screen 1120. The electronic device 201 may identify a wake-up alarm configuration time point as described above according to control by the processor 220.

In an embodiment, the electronic device 201 may perform operation 1030 according to control by the processor 220 when the electronic device 201 has identified that there is a wake-up alarm configured after a current time point. In addition, the electronic device 201 may perform operation 1040 according to control by the processor 220 when the electronic device has identified that there is not wake-up alarm configured after a current time point.

According to an embodiment, in operation 1040, the electronic device 201 may change the operation mode of the electronic device 201 to correspond to the first sleep phase or the sleep-entering phase according to control by the processor 220 as the sleep phase is changed from the second sleep phase or later to the first sleep phase or the sleep-entering phase.

According to an embodiment, in operation 1030, the electronic device (e.g., the electronic device 201) may determine whether a wake-up alarm configuration time point is within a designated hour according to control by the processor 220.

In an embodiment, the designated hour may be predetermined in the electronic device 201 by a user. For example, the designated hour of the electronic device 201 may be 2 hours or 5 hours.

In an embodiment, the electronic device 201 may determine whether the wake-up alarm configuration time point is within a designated hour according to control by the processor 220. For example, when the designated hour of the electronic device 201 is 2 hours, the electronic device 201 may identify that the wake-up alarm configuration time point is within the designated hour in a case of an alarm screen 1110 as shown in FIG. 11A, and, as shown in FIG. 11B, the electronic device 201 may identify that the wake-up alarm configuration time point is not within the designated hour in a case of an alarm screen 1120.

In an embodiment, the electronic device 201 may perform operation 1040 according to control by the processor 220 when the electronic device has identified that the wake-up alarm configuration time point is within the designated hour, and perform operation 1050 according to control by the processor 220 when the electronic device has identified that the wake-up alarm configuration time point is not within the designated hour.

According to an embodiment, in operation 1040, the electronic device (e.g., the electronic device 201) may change the operation mode to an operation of the first sleep phase or the sleep-entering phase according to control by the processor 220. For example, the electronic device 201 may change the operation mode of the electronic device 201 to correspond to the first sleep phase or the sleep-entering phase according to control by the processor 220 as the sleep phase is changed from the second sleep phase or later to the first sleep phase or the sleep-entering phase.

According to an embodiment, in operation 1050, the electronic device (e.g., the electronic device 201) may maintain the operation mode of the second sleep phase or later according to control by the processor 220. For example, even in a case where the electronic device 201 has identified that the sleep phase is changed from the second sleep phase or later to the first sleep phase or the sleep-entering phase, the electronic device may maintain the operation mode of the second sleep phase or later according to control by the processor 220 when the electronic device has identified that there is a wake-up alarm configured after a current time point and the wake-up alarm configuration time point is not within a designated hour.

Figure 12:
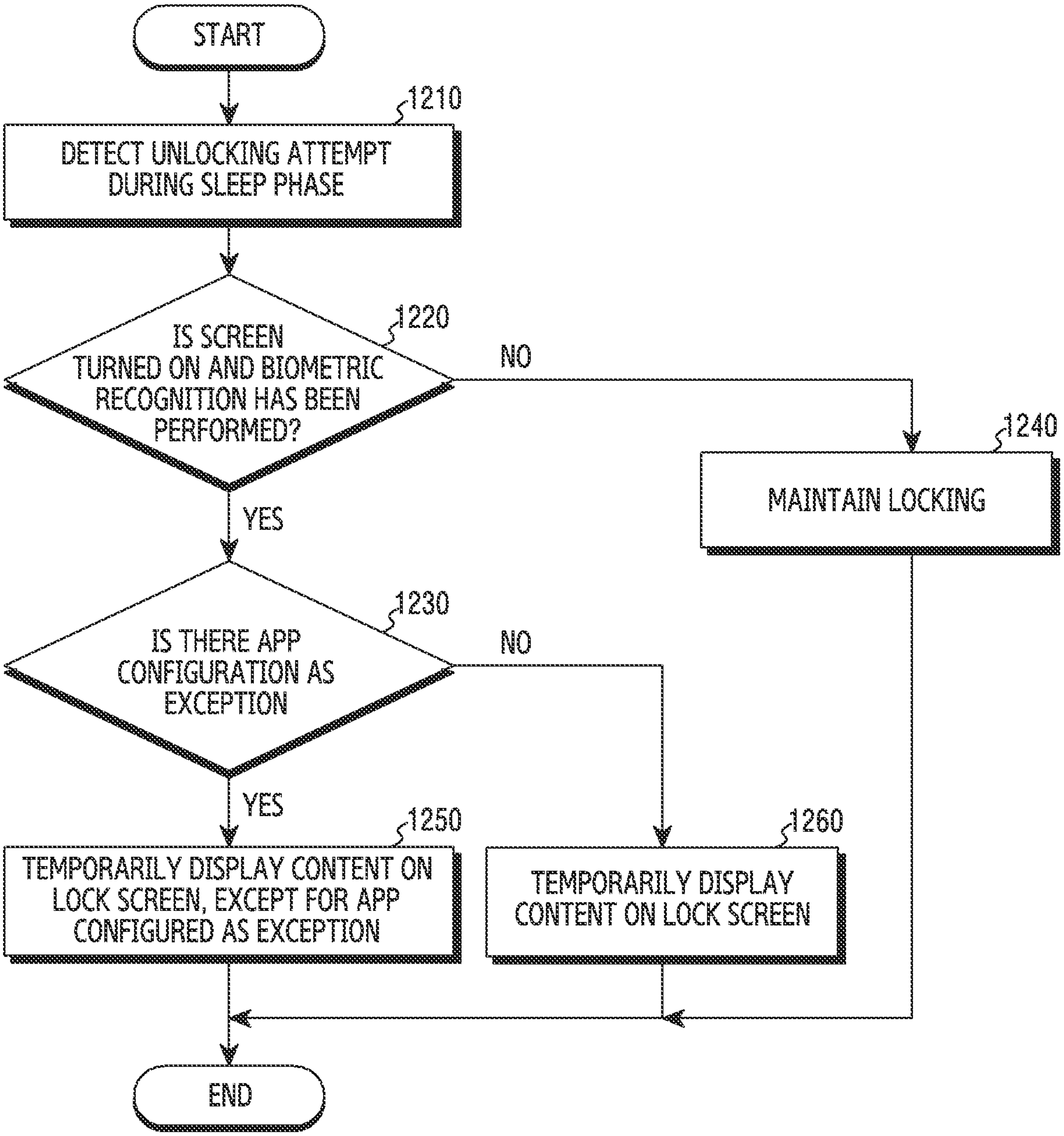
FIG. 12 is a flowchart illustrating an operation in a case where there is an unlocking attempt during a sleep phase in an electronic device according to an embodiment.
Figures 13A, 13B:
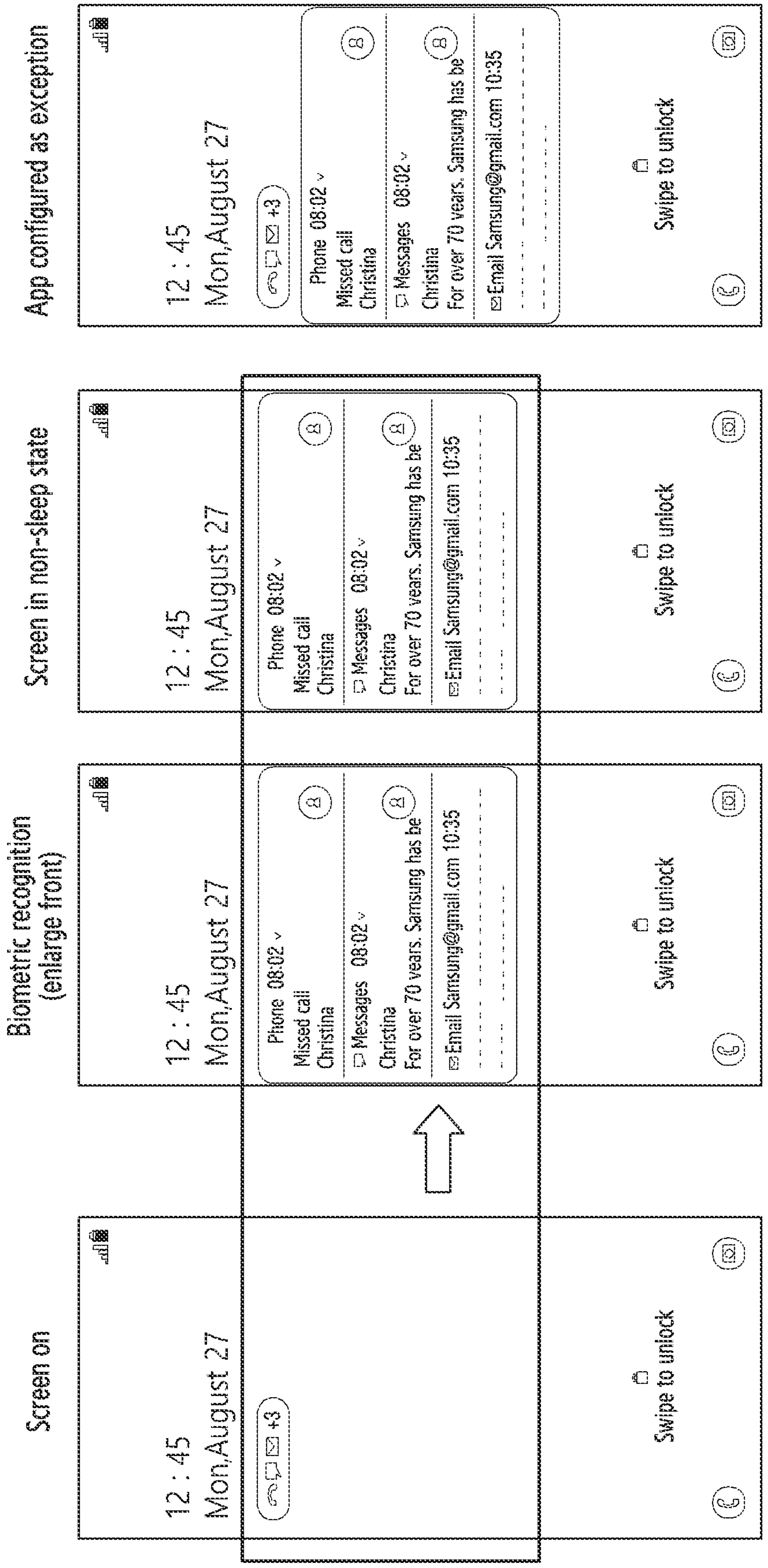
FIG. 13A illustrates a display screen of a case where there is an unlocking attempt during a sleep phase in an electronic device according to an embodiment.
FIG. 13B illustrates a display screen of a case where an app is configured as an exception during a sleep phase in an electronic device according to an embodiment.

FIG. 12 is a flowchart illustrating an operation in a case where there is an unlocking attempt during a sleep phase in an electronic device according to an embodiment. A description of operations 1210 to 1260 of FIG. 12 will be made with reference to FIGS. 13A and 13B illustrating an embodiment of a display screen in a case where there is an unlocking attempt in an electronic device during the sleep phase.

According to an embodiment, in operation 1210, an electronic device (e.g., the electronic device 201) may detect an unlocking attempt during a sleep phase according to control by the processor 220. For example, the electronic device 201 may identify that a user is sleeping, based on sleep data from the external electronic device 111, and determine a specific sleep phase (e.g., a sleep-entering phase, a first sleep phase, and a second sleep phase or later). In addition, the electronic device 201 may detect an unlocking attempt during a specific sleep phase according to control by the processor 220. The unlocking attempt may be, for example, an attempt based on biometric recognition such as fingerprint recognition, iris recognition, and face recognition.

According to an embodiment, in operation 1220, the electronic device (e.g., the electronic device 201) may determine whether a screen is turned on and biometric recognition has been performed. For example, the electronic device 201 may determine whether a display screen is in a screen-on state as shown in a screen 1310 (refer to FIG. 13A), and determine whether biometric recognition for unlocking has been performed in the screen-on state, according to control by the processor 220.

In an embodiment, the electronic device 201 may perform operation 1230 according to control by the processor 220 when the electronic device has determined that the screen is turned on and the biometric recognition has been performed, and may perform operation 1240 according to control by the processor 220 when the electronic device has determined that the screen is not turned on and the biometric recognition has not been performed.

According to an embodiment, in operation 1240, the electronic device 201 may maintain unlocking according to control by the processor 220.

According to an embodiment, in operation 1230, the electronic device (e.g., the electronic device 201) may determine whether there is an app configured as an exception, according to control by the processor 220. For example, the electronic device 201 may have an app configured not to be included in a notification displayed on a screen in a lock screen state, and an app configured to be displayed on the screen. The app displayed in the lock screen state may be configured for the electronic device 201 by a user. The electronic device 201 may identify or determine, according to control by the processor 220, whether there is an app configured as an exception, which is arbitrability configured by the user.

In an embodiment, the electronic device 201 may perform operation 1250 according to control by the processor 220 when the electronic device has identified that there is an app configured as an exception, and perform operation 1260 according to control by the processor 220 when the electronic device has identified that there is no app configured as an exception.

According to an embodiment, in operation 1250, the electronic device (e.g., the electronic device 201) may temporarily display, according to control by the processor 220, a content on a lock screen, except for the app configured as an exception.

In an embodiment, as identifying that there is an app configured as an exception, the electronic device 201 may temporarily display, according to control by the processor 220, a content (e.g., a notification) on a lock screen, except for the app configured as an exception. In addition, when displaying a content (e.g., a notification) according to control by the processor 220, the electronic device 201 may display the content (e.g., the notification) while temporarily enlarging the font so that the user can conveniently check the content upon biometric recognition. For example, the electronic device 201 may display the content in a normal font size as shown in a screen 1330 when the user is not sleeping, and temporarily display the content in a larger font than the normal font size as shown in a screen 1320 when the user is sleeping, according to control by the processor 220 (refer to FIG. 13A). In addition, the electronic device 201 may display, according to control by the processor 220, the content as shown in a screen 1340 so that contents of the notification of the app configured as an exception is not displayed as shown in FIG. 13B.

According to an embodiment, in operation 1260, the electronic device (e.g., the electronic device 201) may temporarily display the content on the lock screen according to control by the processor 220. For example, as identifying that there is no app configured as an exception, the electronic device 201 may temporarily display the content (e.g., the notification) on the lock screen without limitation according to control by the processor 220.

Figure 14:
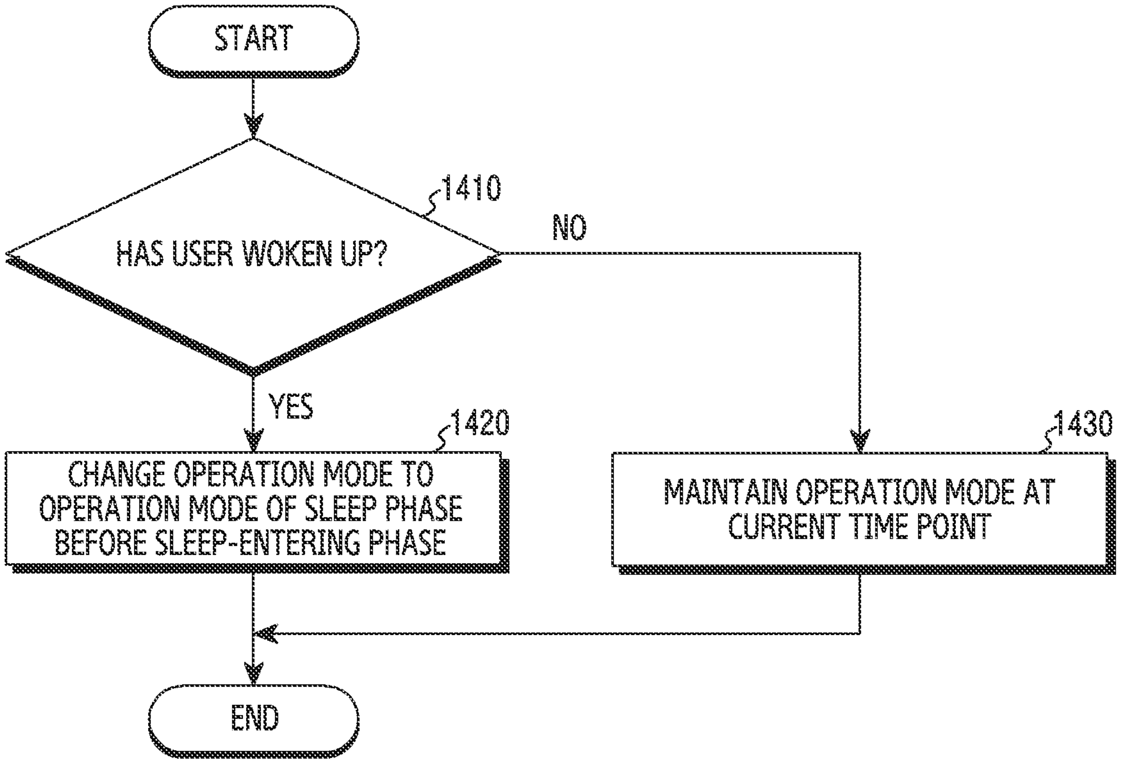
FIG. 14 is a flowchart illustrating an operation in a case where a user wakes up during a sleep phase in an electronic device according to an embodiment.

FIG. 14 is a flowchart illustrating an operation in a case where a user wakes up during a sleep phase in an electronic device according to an embodiment.

According to an embodiment, in operation 1410, an electronic device (e.g., the electronic device 201) may determine whether a user has woken up, according to control by the processor 220.

In an embodiment, the electronic device 201 may acquire the user's sleep data acquired by the external electronic device 111 by using the photoplethysmography scheme. The electronic device 201 may determine whether the user has woken up, based on the acquired sleep data according to control by the processor 220.

In an embodiment, the electronic device 201 may perform operation 1420 according to control by the processor 220 when the electronic device has determined that the user has woken up. In addition, the electronic device 201 perform operation 1430 of maintaining an operation mode at a current time point according to control by the processor 220 when the electronic device has determined that the user has not woken up.

According to an embodiment, in operation 1420, the electronic device (e.g., the electronic device 201) may change the operation mode to an operation mode of a phase before a sleep-entering phase, according to control by the processor 220. For example, the electronic device 201 may change the operation mode to the operation mode of the phase before the sleep-entering phase according to control by the processor 220 when the electronic device has determined that the user has woken up.

According to an embodiment, in operation 1430, the electronic device (e.g., the electronic device 201) may maintain the operation mode at the current time point according to control by the processor 220. For example, the electronic device 201 may maintain one of specific sleep phases (e.g., the sleep-entering phase, the first sleep phase, and the second sleep phase) according to control by the processor 220 when the electronic device has determined that the user has not woken up.

Figure 15A:
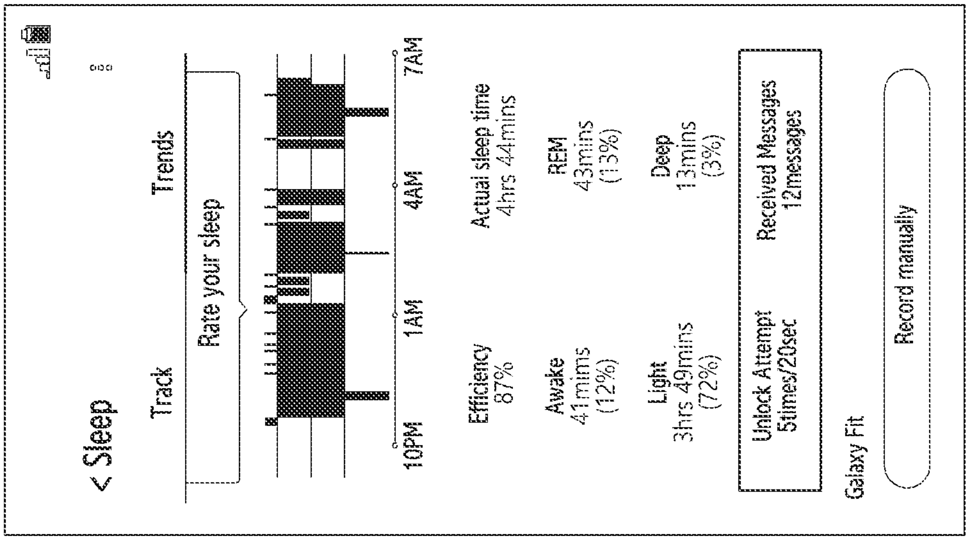
FIG. 15A illustrates a first display screen after a user wakes up when there is an unlocking attempt during a sleep phase in an electronic device according to an embodiment.
Figure 15B:
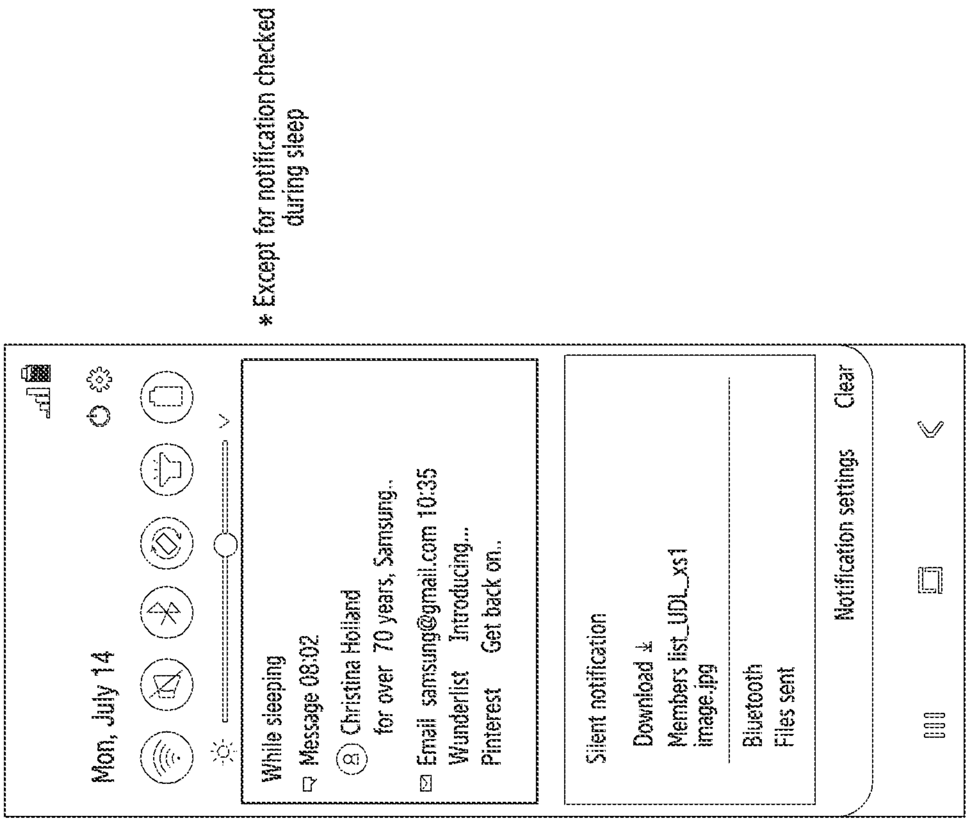
FIG. 15B illustrates a second display screen after a user wakes up when there is an unlocking attempt during a sleep phase in an electronic device according to an embodiment.

FIGS. 15A and 15B illustrate a first display screen and a second display screen, respectively, after a user wakes up when there is an unlocking attempt during a sleep phase in an electronic device according to an embodiment.

As shown in FIG. 15A, in an embodiment, the electronic device 201 may provide, according to control by the processor 220, a user with records such as the number of unlocking attempts and the number of received messages through a display screen after the user wakes up when there has been an unlocking attempt during a sleep phase.

As shown in FIG. 15B, in an embodiment, after the user wakes up, the electronic device 201 may provide, according to control by the processor 220, the user with records such as the number of unlocking attempts and the number of received messages through the display screen, except for a notification which has been identified during sleep when there has been an unlocking attempt during the sleep phase.

An electronic device (e.g., the electronic device 201) according to an embodiment of the disclosure may include a display (e.g., the display module 260) configured to display a screen, a memory (e.g., the memory 230), and a processor (e.g., the processor 220) electrically connected to the display (e.g., the display module 260) and the memory (e.g., the memory 230), wherein the processor (e.g., the processor 220) is configured to acquire sleep data from an external electronic device (e.g., external electronic device 111), determine a sleep phase, based on the acquired sleep data, identify an operation mode of the electronic device (e.g., the electronic device 201), the operation mode being associated with the determined sleep phase, and in case that the operation mode is identified, configure the electronic device (e.g., the electronic device 201) with the identified operation mode In the electronic device (e.g., the electronic device 201) according to an embodiment of the disclosure, the processor (e.g., the processor 220) may configure different alert strengths according to the sleep phase.

In the electronic device (e.g., the electronic device 201) according to an embodiment of the disclosure, the processor (e.g., the processor 220) may, in case that the sleep phase is determined as a first sleep phase and a notification configuration of a lock screen is a "details" view, change the notification configuration to an "icons only" view.

In the electronic device (e.g., the electronic device 201) according to an embodiment of the disclosure, the processor (e.g., the processor 220) may, in case that the sleep phase is determined as not a first sleep phase, maintain an operation mode of a sleep-entering phase.

In the electronic device (e.g., the electronic device 201) according to an embodiment of the disclosure, the processor (e.g., the processor 220) may, in case that the sleep phase is determined as a first sleep phase and a sound mode configuration is a "Sound" mode or a "Vibrate" mode, change the sound mode configuration to a "Mute" mode.

In the electronic device (e.g., the electronic device 201) according to an embodiment of the disclosure, the processor (e.g., the processor 220), responsive to the sleep phase being determined as a second sleep phase or later, may or may not perform unlocking according to whether an unlocking configuration based on biometric recognition is made.

In the electronic device (e.g., the electronic device 201) according to an embodiment of the disclosure, the processor (e.g., the processor 220) may, in case that the sleep phase is changed from a second sleep phase or later to a first sleep phase or a sleep-entering phase, maintain an operation mode of the second sleep phase or later, or change the operation mode to an operation mode of the first sleep phase or the sleep-entering phase, according to whether there is a wake-up alarm configured after a current time point.

In the electronic device (e.g., the electronic device 201) according to an embodiment of the disclosure, the processor (e.g., the processor 220) may, in case that an unlocking attempt is detected during the sleep phase, temporarily display a content on a lock screen, except for any apps configured as an exception when there is at least one app configured as an exception, and temporarily display a content on a lock screen without limitation in case that there are no apps configured as an exception.

In the electronic device (e.g., the electronic device 201) according to an embodiment of the disclosure, the processor (e.g., the processor 220) may maintain locking in case that an unlocking attempt is detected during the sleep phase and determination is made that a screen is not turned on and biometric recognition has not been performed.

In the electronic device (e.g., the electronic device 201) according to an embodiment of the disclosure, the processor (e.g., the processor 220) may change the operation mode to an operation mode of a phase before a sleep-entering phase in case that a user wakes up during the sleep phase, and maintain an operation mode at a current time point in case that a user does not wake up during the sleep phase.

An operation method of an electronic device (e.g., the electronic device 201) according to an embodiment of the disclosure may include: acquiring sleep data from an external electronic device (e.g., external electronic device 111), determining a sleep phase, based on the acquired sleep data, identifying an operation mode of the electronic device (e.g., the electronic device 201), the operation mode being associated with the determined sleep phase, and in case that the operation mode is identified, configuring the electronic device (e.g., the electronic device 201) with the identified operation mode.

The operation method of the electronic device (e.g., the electronic device 201) according to an embodiment of the disclosure may include configuring different alert strengths according to the sleep phase.

The operation method of the electronic device (e.g., the electronic device 201) according to an embodiment of the disclosure may include determining the sleep phase as a first sleep phase, and in case that a notification configuration of a lock screen is a "details" view, changing the notification configuration to an "icons only" view.

The operation method of the electronic device (e.g., the electronic device 201) according to an embodiment of the disclosure may include determining that the sleep phase is not a first sleep phase, and maintaining an operation mode of a sleep-entering phase.

The operation method of the electronic device (e.g., the electronic device 201) according to an embodiment of the disclosure may include determining the sleep phase as a first sleep phase, and in case that a sound mode configuration is a "Sound" mode or a "Vibrate" mode, changing the sound mode configuration to a "Mute" mode.

The operation method of the electronic device (e.g., the electronic device 201) according to an embodiment of the disclosure may include determining the sleep phase as a second sleep phase or later, and performing or not performing unlocking according to whether an unlocking configuration based on biometric recognition is made.

The operation method of the electronic device (e.g., the electronic device 201) according to an embodiment of the disclosure may include changing the sleep phase from a second sleep phase or later to a first sleep phase or a sleep-entering phase, and maintaining an operation mode of the second sleep phase or later, or changing the operation mode to an operation mode of the first sleep phase or the sleep-entering phase, according to whether there is a wake-up alarm configured after a current time point.

The operation method of the electronic device (e.g., the electronic device 201) according to an embodiment of the disclosure may include detecting an unlocking attempt during the sleep phase, temporarily displaying a content on a lock screen, except for an app configured as an exception in case that there is the app configured as an exception, and temporarily displaying a content on a lock screen without limitation in case that there is no app configured as an exception.

The operation method of the electronic device (e.g., the electronic device 201) according to an embodiment of the disclosure may include detecting an unlocking attempt during the sleep phase, and maintaining locking in case that determination is made that a screen is not turned on and biometric recognition has not been performed.

The operation method of the electronic device (e.g., the electronic device 201) according to an embodiment of the disclosure may include changing the operation mode to an operation mode of a phase before a sleep-entering phase in case that a user wakes up during the sleep phase, and maintaining an operation mode at a current time point in case that a user does not wake up during the sleep phase.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 240) including one or more instructions that are stored in a storage medium (e.g., internal memory 236 or external memory 238) that is readable by a machine (e.g., the electronic device 201). For example, a processor (e.g., the processor 220) of the machine (e.g., the electronic device 201) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

The invention claimed is:

1. An electronic device comprising:
- a display;
- memory;
- at least one processor; and
- communication circuitry;
- wherein the memory stores instructions that, when executed by the at least one processor, cause the electronic device to:
  - acquire, via the communication circuitry, sleep data from an external electronic device;
  - determine a sleep phase, based on the sleep data; and
  - while the sleep phase corresponds to a second sleep phase or later after one of a first sleep phase and a sleep-entering phase, responsive to detecting an unlocking attempt for the electronic device, block unlocking or perform unlocking according to whether an unlocking configuration based on biometric recognition is made.

2. The electronic device of claim 1, wherein the instructions that, when executed by the at least one processor, cause the electronic device to configure different alert strengths according to the sleep phase.

3. The electronic device of claim 1, wherein the instructions that, when executed by the at least one processor, cause the electronic device to, responsive to the sleep phase comprising the first sleep phase and a notification configuration of a lock screen comprising a details view, change the notification configuration to an icons-only view.

4. The electronic device of claim 1, wherein the instructions that, when executed by the at least one processor, cause the electronic device to, responsive to the sleep phase not comprising the first sleep phase, maintain an operation mode of a sleep-entering phase.

5. The electronic device of claim 1, wherein the instructions that, when executed by the at least one processor, cause the electronic device to, responsive to the sleep phase comprising the first sleep phase and a sound mode configuration comprising one of a sound mode or a vibrate mode, change the sound mode configuration to a mute mode.

6. The electronic device of claim 1, wherein the instructions that, when executed by the at least one processor, cause the electronic device to, responsive to the sleep phase changing from the second sleep phase or later to one of the first sleep phase and the sleep-entering phase, maintain an operation mode of the second sleep phase or later, or change the operation mode to an operation mode of the first sleep phase or the sleep-entering phase, according to whether there is a wake-up alarm configured after a current time point.

7. The electronic device of claim 1, wherein the instructions that, when executed by the at least one processor, cause the electronic device to, responsive to detecting an unlocking attempt during the sleep phase:
- temporarily display a content on a lock screen, except for any app configured as an exception, responsive to there existing at least one app configured as an exception; and
- temporarily display a content on a lock screen without limitation, responsive to no apps being configured as an exception.

8. The electronic device of claim 1, wherein the instructions that, when executed by the at least one processor, cause the electronic device to maintain locking responsive to detecting an unlocking attempt during the sleep phase and determining that a screen is not turned on and biometric recognition has not been performed.

9. The electronic device of claim 1, wherein the instructions that, when executed by the at least one processor, cause the electronic device to:
- change an operation mode to an operation mode of a phase before a sleep-entering phase responsive to a user waking up during the sleep phase; and
- maintain an operation mode at a current time point responsive to a user remaining asleep during the sleep phase.

10. An operating method of an electronic device, the method comprising:
- acquiring sleep data from an external electronic device;
- determining a sleep phase, based on the sleep data; and
- while the sleep phase corresponds to a second sleep phase or later after one of a first sleep phase and a sleep-entering phase, responsive to detecting an unlocking attempt for the electronic device, blocking unlocking or performing unlocking according to whether an unlocking configuration based on biometric recognition is made.

11. The method of claim 10, further comprising configuring different alert strengths according to the sleep phase.

12. The method of claim 10, further comprising:
- determining the sleep phase is the first sleep phase; and
- in case that a notification configuration of a lock screen is a details view, changing the notification configuration to an icons-only view.

13. The method of claim 10, further comprising:
- determining the sleep phase is the first sleep phase; and responsive to a sound mode configuration comprising a sound mode or a vibrate mode, changing the sound mode configuration to a mute mode.

14. The method of claim 10, further comprising:

changing the sleep phase from the second sleep phase or later to the first sleep phase or the sleep-entering phase; and maintaining an operation mode of the second sleep phase or later, or changing the operation mode to an operation mode of the first sleep phase or the sleep-entering phase, according to whether there is a wake-up alarm configured after a current time point.

15. The method of claim 10, further comprising:

detecting an unlocking attempt during the sleep phase;

displaying content on a lock screen, except for an app configured as an exception in case that there is the app configured as an exception; and displaying content on a lock screen without limitation in case that there is no app configured as an exception.

16. The method of claim 10, further comprising:

detecting an unlocking attempt during the sleep phase; and maintaining locking in case that determination is made that a screen is not turned on and biometric recognition has not been performed.

17. The method of claim 10, further comprising:

changing an operation mode to an operation mode of a phase before a sleep-entering phase in case that a user wakes up during the sleep phase; and maintaining an operation mode at a current time point in case that a user does not wake up during the sleep phase.

18. The method of claim 10, further comprising:

determining that the sleep phase is not a first sleep phase; and maintaining an operation mode of a sleep-entering phase.

19. An electronic device comprising:

a display;

memory;

at least one processor; and communication circuitry;

wherein the memory stores instructions that, when executed by the at least one processor, cause the electronic device to:

acquire, via the communication circuitry, sleep data from an external electronic device;

determine a sleep phase, based on the sleep data; and responsive to the sleep phase comprising a first sleep phase and a notification configuration of a lock screen comprising a details view, change the notification configuration to an icons only view.

20. The electronic device of claim 19, wherein the instructions that, when executed by the at least one processor, cause the electronic device to, responsive to the sleep phase not comprising the first sleep phase, maintain an operation mode of a sleep-entering phase.

* * * * *